(12) United States Patent
Sahin et al.

(10) Patent No.: US 8,088,913 B2
(45) Date of Patent: Jan. 3, 2012

(54) COMPOSITIONS AND METHODS FOR THERAPY AND DIAGNOSIS OF CANCER

(75) Inventors: Ugur Sahin, Mainz (DE); Özlem Türeci, Mainz (DE); Michael Koslowski, Mainz (DE)

(73) Assignees: Ganymed Pharmaceuticals AG, Mainz (DE); Johannes Gutenberg-Universitat Mainz, Mainz (DE)

( * ) Notice: Subject to any disclaimer, the term of this patent is extended or adjusted under 35 U.S.C. 154(b) by 32 days.

(21) Appl. No.: 12/096,216

(22) PCT Filed: Dec. 7, 2006

(86) PCT No.: PCT/EP2006/011785
§ 371 (c)(1),
(2), (4) Date: Oct. 14, 2008

(87) PCT Pub. No.: WO2007/065690
PCT Pub. Date: Jun. 14, 2007

(65) Prior Publication Data
US 2009/0221674 A1 Sep. 3, 2009

(30) Foreign Application Priority Data
Dec. 8, 2005 (EP) ..................... 05026874

(51) Int. Cl.
C07H 21/04 (2006.01)
C07H 21/02 (2006.01)
C12N 15/63 (2006.01)
A61K 48/00 (2006.01)

(52) U.S. Cl. ................... 536/24.5; 536/23.1; 435/320.1; 514/44

(58) Field of Classification Search ........................ None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 2002/0086356 A1 | 7/2002 | Tuschl et al. | |
| 2005/0203043 A1* | 9/2005 | Fedorov et al. | 514/44 |
| 2008/0113351 A1* | 5/2008 | Naito et al. | 435/6 |

FOREIGN PATENT DOCUMENTS

| WO | WO 92/04381 | 3/1992 |
|---|---|---|
| WO | WO 2005026205 | 3/2005 |

OTHER PUBLICATIONS

U.S. Appl. No. 10/570,957, filed Mar. 10, 2006, Tureci et al.
Szoka et al., Ann. Rev. Biophys. Bioeng., (1980) 9:457.
Fire et al., Nature, (1998) 391:806-811.
Elbashir et al., Genes Dev., (2001) 15:188-200.
Elbashir et al., Nature, (2001) 411:494-498.
McCaffrey et al., Nature, (2002) 418:38-39.
Xia et al., Nat. Biotech., (2002) 20:1006-1010.
Novina et al., Nat. Med. (2002) 8:681-686.
Clark et al., Nucleic Acids Res., (1994) 22(15):2990-7 (1994).
Sambrook et al, Molecular Cloning: A Laboratory Manual, 2nd Ed., (1989) Cold Spring Harbor Laboratory Press, Cold Spring Harbor, New York.
Ausubel et al., Current Protocols in Molecular Biology, John Wiley & Sons, Inc., New York.
Neddleman and Wunsch, J. Mol. Biol., (1970) 48, 443.
Pearson and Lipman, Proc. Nat'l Acad. Sci. USA, (1988) 85, 2444.
Tuschl et al., "The siRNA User Guide", available at http://www.rockefeller.edu/labheads/tuschl/sirna.html.
Shepherd, "Monoclonal Antibodies: A Practical Approach", Christopher Dean: ISBN 0-19-963722-9.
Harlow, "Antibodies: A Laboratory Manual", David Lane ISBN: 0879693142.
Harlow and Lane, "Using Antibodies: A Laboratory Manual: Portable Protocol NO", Ed Harlow: ISBN 0879695447.
Azorsa et al, J. Immunol. Methods, (1999) 229:35-48.
Anderson et al., J. Immunol., (1989) 143:1899-1904.
Gardsvoll, J. Immunol. Methods, (2000) 234:107-116.
Clark, The Experimental Foundations of Modern Immunology (1986) Wiley & Sons, Inc., New York.
Roitt, Essential Immunology, 7th Ed., (1991) Blackwell Scientific Publications, Oxford.
Koslowski et al., Cancer Res., (2002) 62, 6750-6755.
Koslowski et al., Cancer Res., (2004) 64, 5988-5993.
Tall et al., Curr. Biol., (2000) 10, 743-746.
Watton & Downward, Curr. Biol., (1999) 9, 433-436.
Voura et al., Nat. Med. (2004), 10, 993-998.
Wu et al., J. Biol. Chem., (2001) 276, 21745-21753.
De Smet et al., Mol. Cell Biol. (1999) 19, 7327-7335.
De Smet et al., Mol. Cell Biol. (2004) 24, 4781-4790.
Ehrlich, Oncogene (2002) 21, 5400-5413.
Feinberg & Vogelstein, Nature (1983) 301, 89-92.
Lee et al., Cell (1999) 99, 323-334.
Schiffer et al., Cancer Res., (2003) 63, 7221-7231.
Iijima et al., J. Biol. Chem, (2004) 279, 16606-16613.
McCulloch et al., Eur. J. Surg. Oncol., (1997) 23, 304-309.
Price et al., Cancer Res. (1999) 59, 5475-5478.
Heldin & Westermark, Physiol Rev. (1999) 79, 1283-1316.
Muller et al., Nature, (2001) 410, 50-56.
Ahr, et al., Lancet, (2002) 359, 131-132.
Extended European Search Report for Application No. 05026874.7.
International Search Report for Application No. PCT/EP2006/011785.
Written Opinion of the International Searching Authority for Application No. PCT/EP2006/011785.

* cited by examiner

*Primary Examiner* — Amy Bowman
(74) *Attorney, Agent, or Firm* — McAndrews, Held & Malloy Ltd.

(57) ABSTRACT

The present invention is directed to siRNA molecules which specifically target and cause RNAi-induced degradation of mRNA from TPTE genes, so that the protein product of the TPTE gene is not produced or is produced in reduced amounts. The siRNA compounds and compositions of the invention are useful for treating diseases which require inhibition of TPTE expression for their treatment, in particular cancer pathologies. The present invention also includes methods which make possible to assess and/or prognose the metastatic behavior of a cancer disease and/or the occurrence of a relapse of cancer.

21 Claims, 6 Drawing Sheets

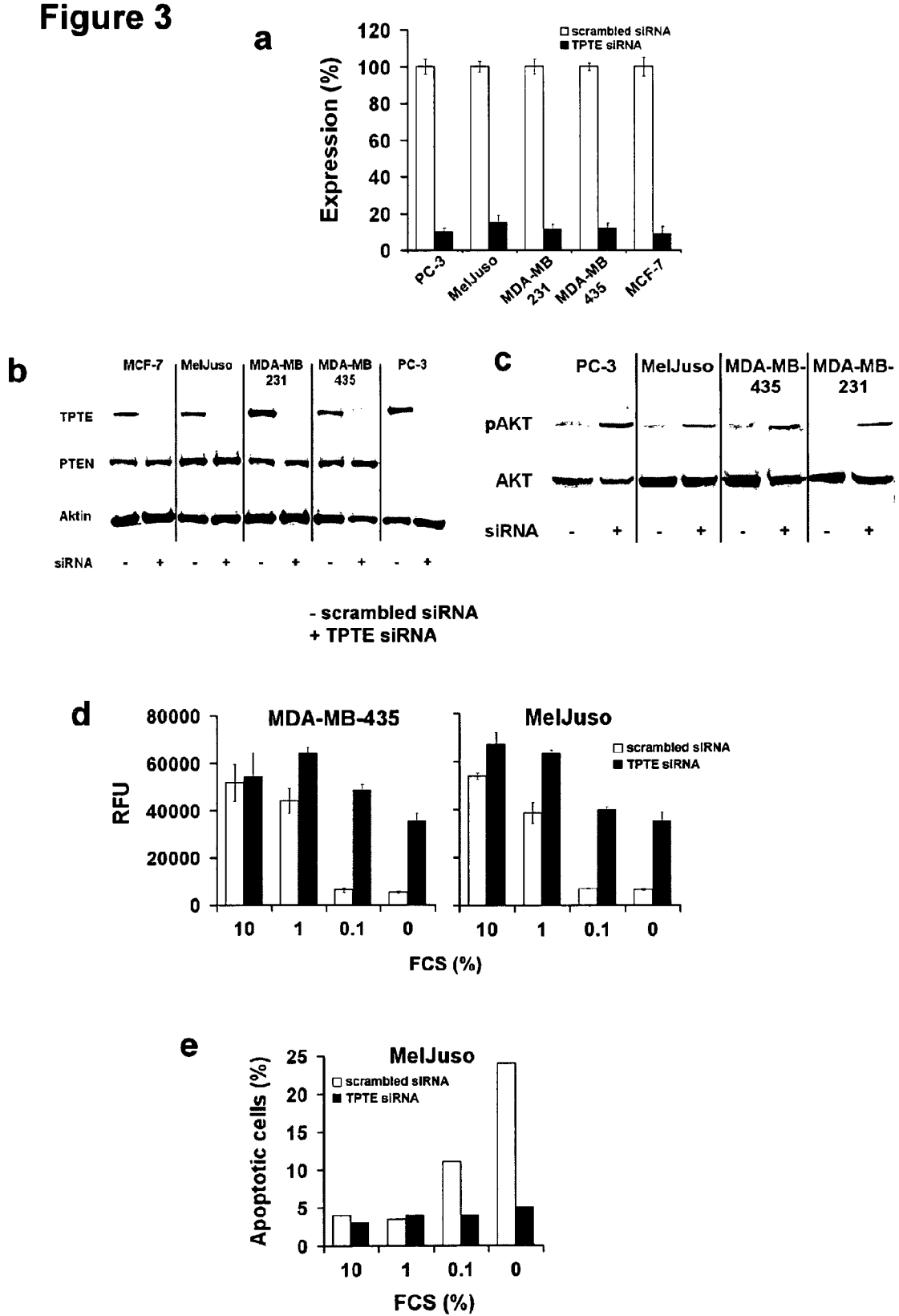

SEQUENCE LISTING

```
<160> NUMBER OF SEQ ID NOS: 46

<210> SEQ ID NO 1
<211> LENGTH: 2168
<212> TYPE: DNA
<213> ORGANISM: Homo sapiens

<400> SEQUENCE: 1
gaatccgcgg ggagggcaca acagctgcta cctgaacagt ttctgaccca acagttaccc      60
agcgccggac tcgctgcgcc ccggcggctc tagggacccc cggcgcctac acttagctcc     120
gcgcccgaga gaatgttgga ccgacgacac aagacctcag acttgtgtta ttctagcagc     180
tgaacacacc ccaggctctt ctgaccggca gtggctctgg aagcagtctg gtgtatagag     240
ttatggattc actaccagat tctactgtat gctcttgaca actatgacca caatggtcca     300
cccacaaatg aattatcagg agtgaaccca gaggcacgta tgaatgaaag tcctgatccg     360
actgacctgg cgggagtcat cattgagctc ggccccaatg acagtccaca gacaagtgaa     420
tttaaaggag caaccgagga ggcacctgcg aaagaaagcc cacacacaag tgaatttaaa     480
ggagcagccc gggtgtcacc tatcagtgaa agtgtgttag cacgactttc caagtttgaa     540
gttgaagatg ctgaaaatgt tgcttcatat gacagcaaga ttaagaaaat tgtgcattca     600
attgtatcat cctttgcatt tggactattt ggagttttcc tggtcttact ggatgtcact     660
ctcatccttg ccgacctaat tttcactgac agcaaacttt atattccttt ggagtatcgt     720
tctatttctc tagctattgc cttatttttt ctcatggatg ttcttcttcg agtatttgta     780
gaaaggagac agcagtattt ttctgactta tttaacattt tagatactgc cattattgtg     840
attcttctgc tggttgatgt cgtttacatt ttttttgaca ttaagttgct taggaatatt     900
cccagatgga cacatttact tcgacttcta cgacttatta ttctgttaag aatttttcat     960
ctgtttcatc aaaaaagaca acttgaaaag ctgataagaa ggcgggtttc agaaaacaaa    1020
aggcgataca caagggatgg atttgaccta gacctcactt acgttacaga acgtattatt    1080
gctatgtcat ttccatcttc tggaaggcag tctttctata gaaatccaat caaggaagtt    1140
```

```
gtgcggtttc tagataagaa acaccgaaac cactatcgag tctacaatct atgcagtgaa    1200
agagcttacg atcctaagca cttccataat agggtcgtta gaatcatgat tgatgatcat    1260
aatgtcccca ctctacatca gatggtggtt ttcaccaagg aagtaaatga gtggatggct    1320
caagatcttg aaaacatcgt agcgattcac tgtaaaggag gcacagatag aacaggaact    1380
atggtttgtg ccttccttat tgcctctgaa atatgttcaa ctgcaaagga aagcctgtat    1440
tattttggag aaaggcgaac agataaaacc cacagcgaaa aatttcaggg agtagaaact    1500
ccttctcaga agagatatgt tgcatatttt gcacaagtga acatctcta caactggaat    1560 ctccctccaa gacggatact ctttataaaa cacttcatta tttattcgat tcctcgttat    1620
gtacgtgatc taaaaatcca aatagaaatg gagaaaaagg ttgtcttttc cactatttca    1680
ttaggaaaat gttcggtact tgataacatt acaacagaca aaatattaat tgatgtattc    1740
gacggtccac ctctgtatga tgatgtgaaa gtgcagtttt tctattcgaa tcttcctaca    1800
tactatgaca attgctcatt ttacttctgg ttgcacacat ctttattga aaataacagg    1860 ctttatctac aaaaaatga attggataat ctacataaac aaaaagcacg gagaatttat    1920
ccatcagatt tgccgtggga gatactttt ggcgagaaaa tgacttccag tgatgttgta    1980
gctggatccg attaagtata gctccccctt cccttctgg gaagaatta tgttctttcc    2040 aaccctgcca catgttcata tatcctaaat ctatcctaaa tgttcccttg aagtatttat    2100
ttatgtttat atatgtttat acatgttctt caataaatct attacatata tataaaaaaa    2160
aaaaaaaa                                                              2168

<210> SEQ ID NO 2
<211> LENGTH: 2114
<212> TYPE: DNA
<213> ORGANISM: Homo sapiens

<400> SEQUENCE: 2
gaatccgcgg ggagggcaca acagctgcta cctgaacagt ttctgaccca acagttaccc      60
agcgccggac tcgctgcgcc ccggcggctc tagggacccc cggcgcctac acttagctcc     120
gcgcccgaga gaatgttgga ccgacgacac aagacctcag acttgtgtta ttctagcagc     180
tgaacacacc ccaggctctt ctgaccggca gtggctctgg aagcagtctg gtgtatagag     240
ttatggattc actaccagat tctactgtat gctcttgaca actatgacca caatggtcca     300
cccacaaatg aattatcagg agtgaaccca gaggcacgta tgaatgaaag tcctgatccg     360
actgacctgg cggagtcat cattgagctc ggccccaatg cagtccaca gacaagtgaa     420 tttaaaggag caaccgagga ggcacctgcg aaagaaagtg tgttagcacg actttccaag     480
tttgaagttg aagatgctga aaatgttgct tcatatgaca gcaagattaa gaaaattgtg     540
cattcaattg tatcatcctt tgcatttgga ctatttggag ttttcctggt cttactggat     600
gtcactctca tccttgccga cctaatttc actgacagca aacttatat tcctttggag     660 tatcgttcta tttctctagc tattgcctta tttttttctca tggatgttct tcttcgagta     720
tttgtagaaa ggagacagca gtatttttct gacttattta acattttaga tactgccatt     780
attgtgattc ttctgctggt tgatgtcgtt tacatttttt ttgacattaa gttgcttagg     840
aatattccca gatggacaca tttacttcga cttctacgac ttattattct gttaagaatt     900
tttcatctgt ttcatcaaaa aagacaactt gaaaagctga tagaaggcg ggtttcagaa     960 aacaaaaggc gatacacaag ggatggattt gacctagacc tcacttacgt tacagaacgt    1020
attattgcta tgtcatttcc atcttctgga aggcagtctt tctatagaaa tccaatcaag    1080
```

-continued

| | |
|---|---|
| gaagttgtgc ggtttctaga taagaaacac cgaaaccact atcgagtcta caatctatgc | 1140 |
| agtgaaagag cttacgatcc taagcacttc cataataggg tcgttagaat catgattgat | 1200 |
| gatcataatg tccccactct acatcagatg gtggttttca ccaaggaagt aaatgagtgg | 1260 |
| atggctcaag atcttgaaaa catcgtagcg attcactgta aaggaggcac agatagaaca | 1320 |
| ggaactatgg tttgtgcctt ccttattgcc tctgaaatat gttcaactgc aaaggaaagc | 1380 |
| ctgtattatt ttggagaaag gcgaacagat aaaacccaca cgcgaaaatt tcagggagta | 1440 |
| gaaactcctt ctcagaagag atatgttgca tattttgcac aagtgaaaca tctctacaac | 1500 |
| tggaatctcc ctccaagacg gatactcttt ataaaacact tcattattta ttcgattcct | 1560 |
| cgttatgtac gtgatctaaa atccaaata gaaatggaga aaaaggttgt cttttccact | 1620 |
| atttcattag gaaaatgttc ggtacttgat aacattacaa cagacaaaat attaattgat | 1680 |
| gtattcgacg gtccacctct gtatgatgat gtgaaagtgc agttttttcta ttcgaatctt | 1740 |
| cctacatact atgacaattg ctcatttttac ttctggttgc acacatcttt tattgaaaat | 1800 |
| aacaggcttt atctaccaaa aaatgaattg gataatctac ataaacaaaa agcacggaga | 1860 |
| atttatccat cagattttgc cgtggagata cttttttggcg agaaaatgac ttccagtgat | 1920 |
| gttgtagctg gatccgatta agtatagctc ccccttcccc ttctgggaaa gaattatgtt | 1980 |
| cttttccaacc ctgccacatg ttcatatatc ctaaatctat cctaaatgtt cccttgaagt | 2040 |
| atttatttat gtttatatat gtttatacat gttcttcaat aaatctatta catatatata | 2100 |
| aaaaaaaaaa aaaa | 2114 |

<210> SEQ ID NO 3
<211> LENGTH: 2222
<212> TYPE: DNA
<213> ORGANISM: Homo sapiens

<400> SEQUENCE: 3

| | |
|---|---|
| gaatccgcgg ggagggcaca acagctgcta cctgaacagt ttctgaccca acagttaccc | 60 |
| agcgccggac tcgctgcgcc ccggcggctc tagggacccc cggcgcctac acttagctcc | 120 |
| gcgcccgaga gaatgttgga ccgacgacac aagacctcag acttgtgtta ttctagcagc | 180 |
| tgaacacacc ccaggctctt ctgaccggca gtggctctgg aagcagtctg gtgtatagag | 240 |
| ttatggattc actaccagat tctactgtat gctcttgaca actatgacca caatggtcca | 300 |
| cccacaaatg aattatcagg agtgaaccca gaggcacgta tgaatgaaag tcctgatccg | 360 |
| actgacctgg cgggagtcat cattgagctc ggccccaatg acagtccaca gacaagtgaa | 420 |
| tttaaaggag caaccgagga ggcacctgcg aaagaaagcc cacacacaag tgaatttaaa | 480 |
| ggagcagccc gggtgtcacc tatcagtgaa agtgtgttag cacgactttc caagtttgaa | 540 |
| gttgaagatg ctgaaaatgt tgcttcatat gacagcaaga ttaagaaaat tgtgcattca | 600 |
| attgtatcat cctttgcatt tggactattt ggagttttcc tggtcttact ggatgtcact | 660 |
| ctcatccttg ccgacctaat tttcactgac agcaaacttt atattccttt ggagtatcgt | 720 |
| tctatttctc tagctattgc cttattttt ctcatggatg ttcttcttcg agtatttgta | 780 |
| gaaaggagac agcagtattt ttctgactta tttaacattt tagatactgc cattattgtg | 840 |
| attcttctgc tggttgatgt cgtttacatt tttttttgaca ttaagttgct taggaatatt | 900 |
| cccagatgga cacatttact tcgacttcta cgacttatta ttctgttaag aatttttcat | 960 |
| ctgtttcatc aaaaaagaca acttgaaaag ctgataagaa ggcgggttc agaaaacaaa | 1020 |
| aggcgataca caagggatgg attgacctta gacctcactt acgttacaga acgtattatt | 1080 |

-continued

```
gctatgtcat ttccatcttc tggaaggcag tctttctata gaaatccaat caaggaagtt      1140
gtgcggtttc tagataagaa acaccgaaac cactatcgag tctacaatct atgcagtatg      1200
tacattactc tatattgtgc tactgtagat agaaaacaga ttactgcacg tgaaagagct      1260
tacgatccta agcacttcca aatagggtc gttagaatca tgattgatga tcataatgtc       1320
```

```
gctatgtcat ttccatcttc tggaaggcag tctttctata gaaatccaat caaggaagtt      1140
gtgcggtttc tagataagaa acaccgaaac cactatcgag tctacaatct atgcagtatg      1200
tacattactc tatattgtgc tactgtagat agaaaacaga ttactgcacg tgaaagagct      1260
tacgatccta agcacttcca aatagggtc  gttagaatca tgattgatga tcataatgtc      1320
cccactctac atcagatggt ggttttcacc aaggaagtaa atgagtggat ggctcaagat      1380
cttgaaaaca tcgtagcgat tcactgtaaa ggaggcacag atagaacagg aactatggtt      1440
tgtgccttcc ttattgcctc tgaaatatgt tcaactgcaa aggaaagcct gtattatttt      1500
ggagaaaggc gaacagataa aacccacagc gaaaaatttc agggagtaga aactccttct      1560
cagaagagat atgttgcata ttttgcacaa gtgaaacatc tctacaactg gaatctccct      1620
ccaagacgga tactctttat aaaacacttc attatttatt cgattcctcg ttatgtacgt      1680
gatctaaaaa tccaaatagaa aatggagaaa aaggttgtct tttccactat ttcattagga     1740
aaatgttcgg tacttgataa cattacaaca gacaaaatat taattgatgt attcgacggt      1800
ccacctctgt atgatgatgt gaaagtgcag ttttctatt  cgaatcttcc tacatactat      1860
gacaattgct cattttactt ctggttgcac acatctttta ttgaaaataa caggcttttat      1920
ctaccaaaaa atgaattgga taatctacat aaacaaaaag cacggagaat ttatccatca      1980
gattttgccg tggagatact ttttggcgag aaaatgactt ccagtgatgt tgtagctgga      2040
tccgattaag tatagctccc ccttcccctt ctgggaaaga attatgttct ttccaaccct      2100
gccacatgtt catatatcct aaatctatcc taaatgttcc cttgaagtat ttatttatgt      2160
ttatatatgt ttatacatgt tcttcaataa atctattaca tatatataaa aaaaaaaaaa      2220
aa                                                                     2222
```

<210> SEQ ID NO 4
<211> LENGTH: 1550
<212> TYPE: DNA
<213> ORGANISM: Homo sapiens

<400> SEQUENCE: 4

```
atgaatgaaa gtcctgatcc gactgacctg gcgggagtca tcattgagct cggccccaat       60
gacagtccac agacaagtga atttaaagga gcaaccgagg aggcacctgc gaaagaaagc      120
ccacacacaa gtgaatttaa aggagcagcc cgggtgtcac ctatcagtga aagtgtgtta      180
gcacgacttt ccaagtttga agttgaagat gctgaaaatg ttgcttcata tgacagcaag      240
attaagaaaa ttgtgcattc aattgtatca tcctttgcat ttggactatt tggagttttc      300
ctggtcttac tggatgtcac tctcatcctt gccgacctaa ttttcactga cagcaaactt      360
tatattcctt tggagtatcg ttctatttct ctagctattg ccttatttttt tctcatggat      420
gttcttcttc gagtatttgt agaaaggaga cagcagtatt tttctgactt atttaacatt      480
ttagatactg ccattattgt gattcttctg ctggttgatg tcgtttacat ttttttttgac      540
attaagttgc ttaggaatat tcccagatgg acacatttac ttcgacttct acgacttatt      600
attctgttaa gaattttttca tctgtttcat caaaaaagac aacttgaaaa gctgataaga      660
aggcgggttt cagaaaacaa aaggcgatac acaagggatg gatttgacct agacctcact      720
tacgttacag aacgtattat tgctatgtca tttccatctt ctggaaggca gtctttctat      780
agaaatccaa tcaaggaagt gtgcggtttt ctagataaga aacaccgaaa ccactatcga      840
gtctacaatc tatgcagtga aagagcttac gatcctaagc acttccataa tagggtcgtt      900
agaatcatga ttgatgatca taatgtcccc actctacatc agatggtggt tttcaccaag      960
```

```
gaagtaaatg agtggatggc tcaagatctt gaaaacatcg tagcgattca ctgtaaagga    1020
ggcacagata gaacaggaac tatggtttgt gccttcctta ttgcctctga aatatgttca    1080
actgcaaagg aaagcctgta ttattttgga gaaaggcgaa cagataaaac ccacagcgaa    1140
aaatttcagg gagtagaaac tccttctcag gttatgtacg tgatctaaaa atccaaatag    1200
aaatggagaa aaaggttgtc ttttccacta tttcattagg aaaatgttcg gtacttgata    1260
acattacaac agacaaaata ttaattgatg tattcgacgg tccacctctg tatgatgatg    1320
tgaaagtgca gttttctat tcgaatcttc ctacatacta tgacaattgc tcattttact    1380
tctggttgca cacatctttt attgaaaata acaggcttta tctaccaaaa aatgaattgg    1440
ataatctaca taaacaaaaa gcacggagaa tttatccatc agattttgcc gtggagatac    1500
tttttggcga gaaaatgact tccagtgatg ttgtagctgg atccgattaa                1550

<210> SEQ ID NO 5
<211> LENGTH: 1407
<212> TYPE: DNA
<213> ORGANISM: Homo sapiens

<400> SEQUENCE: 5
atgaatgaaa gtcctgatcc gactgacctg gcgggagtca tcattgagct cggccccaat     60
gacagtccac agacaagtga atttaaagga gcaaccgagg aggcacctgc gaaagaaagc    120
ccacacacaa gtgaatttaa aggagcagcc cgggtgtcac ctatcagtga agtgtgttta    180
gcacgacttt ccaagtttga agttgaagat gctgaaaatg ttgcttcata tgacagcaag    240
attaagaaaa ttgtgcattc aattgtatca tcctttgcat ttggactatt tggagttttc    300
ctggtcttac tggatgtcac tctcatcctt gccgacctaa ttttcactga cagcaaactt    360
tatattcctt tggagtatcg ttctatttct ctagctattg ccttattttt tctcatggat    420
gttcttcttc gagtatttgt agaaaggaga cagcagtatt tttctgactt atttaacatt    480
ttagatactg ccattattgt gattcttctg ctggttgatg tcgtttacat tttttttgac    540
attaagttgc ttaggaatat tcccagatgg acacatttac ttcgacttct acgacttatt    600
attctgttaa gaattttttca tctgtttcat caaaaaagac aacttgaaaa gctgataaga    660
aggcgggttt cagaaaacaa aaggcgatac acaagggatg gatttgacct agacctcact    720
tacgttacag aacgtattat tgctatgtca tttccatctt ctggaaggca gtctttctat    780
agaaatccaa tcaaggaagt tgtgcggttt ctagataaga acaccgaaa ccactatcga    840 gtctacaatc tatgcagtga aagagcttac gatcctaagc acttccataa tagggtcgtt    900
agaatcatga ttgatgatca taatgtcccc actctacatc agatggtggt tttcaccaag    960
gaagtaaatg agtggatggc tcaagatctt gaaaacatcg tagcgattca ctgtaaagga    1020
ggcacaggtt atgtacgtga tctaaaaatc caaatagaaa tggagaaaaa ggttgtcttt    1080
tccactattt cattaggaaa atgttcggta cttgataaca ttacaacaga caaaatatta    1140
attgatgtat tcgacggtcc acctctgtat gatgatgtga agtgcagtt tttctattcg    1200 aatcttccta catactatga caattgctca ttttacttct ggttgcacac atctttttatt    1260 gaaaataaca ggctttatct accaaaaaat gaattggata atctacataa acaaaaagca    1320
cggagaattt atccatcaga ttttgccgtg gagatacttt ttggcgagaa aatgacttcc    1380
agtgatgttg tagctggatc cgattaa                                         1407

<210> SEQ ID NO 6
<211> LENGTH: 1413
<212> TYPE: DNA
```

<213> ORGANISM: Homo sapiens

<400> SEQUENCE: 6

| | |
|---|---|
| atgaatgaaa gtcctgatcc gactgacctg gcgggagtca tcattgagct cggccccaat | 60 |
| gacagtccac agacaagtga atttaaagga gcaaccgagg aggcacctgc gaaagaaagt | 120 |
| gtgttagcac gactttccaa gtttgaagtt gaagatgctg aaaatgttgc ttcatatgac | 180 |
| agcaagatta gaaaattgt gcattcaatt gtatcatcct ttgcatttgg actatttgga | 240 |
| gttttcctgg tcttactgga tgtcactctc atccttgccg acctaatttt cactgacagc | 300 |
| aaactttata ttcctttgga gtatcgttct atttctctag ctattgcctt attttttctc | 360 |
| atggatgttc ttcttcgagt atttgtagaa aggagacagc agtattttc tgacttattt | 420 |
| aacattttag atactgccat tattgtgatt cttctgctgg ttgatgtcgt ttacattttt | 480 |
| tttgacatta agttgcttag gaatattccc agatggacac atttacttcg acttctacga | 540 |
| cttattattc tgttaagaat ttttcatctg tttcatcaaa aaagacaact tgaaaagctg | 600 |
| ataagaaggc gggtttcaga aacaaaagg cgatacacaa gggatggatt tgacctagac | 660 |
| ctcacttacg ttacagaacg tattattgct atgtcatttc catcttctgg aaggcagtct | 720 |
| ttctatagaa atccaatcaa ggaagttgtg cggtttctag ataagaaaca ccgaaaccac | 780 |
| tatcgagtct acaatctatg cagtgaaaga gcttacgatc ctaagcactt ccataatagg | 840 |
| gtcgttagaa tcatgattga tgatcataat gtccccactc tacatcagat ggtggttttc | 900 |
| accaaggaag taaatgagtg gatggctcaa gatcttgaaa acatcgtagc gattcactgt | 960 |
| aaaggaggca cagatagaac aggaactatg gtttgtgcct tccttattgc ctctgaaata | 1020 |
| tgttcaactg caaaggaaag cctgtattat tttggagaaa ggcgaacaga taaaacccac | 1080 |
| agcgaaaaat tcagggagt agaaactcct tctgtacttg ataacattac aacagacaaa | 1140 |
| atattaattg atgtattcga cggtccacct ctgtatgatg atgtgaaagt gcagtttttc | 1200 |
| tattcgaatc ttcctacata ctatgacaat tgctcatttt acttctggtt gcacacatct | 1260 |
| tttattgaaa ataacaggct ttatctacca aaaaatgaat tggataatct acataaacaa | 1320 |
| aaagcacgga gaatttatcc atcagatttt gccgtggaga tactttttgg cgagaaaatg | 1380 |
| acttccagtg atgttgtagc tggatccgat taa | 1413 |

<210> SEQ ID NO 7
<211> LENGTH: 1353
<212> TYPE: DNA
<213> ORGANISM: Homo sapiens

<400> SEQUENCE: 7

| | |
|---|---|
| atgaatgaaa gtcctgatcc gactgacctg gcgggagtca tcattgagct cggccccaat | 60 |
| gacagtccac agacaagtga atttaaagga gcaaccgagg aggcacctgc gaaagaaagt | 120 |
| gtgttagcac gactttccaa gtttgaagtt gaagatgctg aaaatgttgc ttcatatgac | 180 |
| agcaagatta gaaaattgt gcattcaatt gtatcatcct ttgcatttgg actatttgga | 240 |
| gttttcctgg tcttactgga tgtcactctc atccttgccg acctaatttt cactgacagc | 300 |
| aaactttata ttcctttgga gtatcgttct atttctctag ctattgcctt attttttctc | 360 |
| atggatgttc ttcttcgagt atttgtagaa aggagacagc agtattttc tgacttattt | 420 |
| aacattttag atactgccat tattgtgatt cttctgctgg ttgatgtcgt ttacattttt | 480 |
| tttgacatta agttgcttag gaatattccc agatggacac atttacttcg acttctacga | 540 |
| cttattattc tgttaagaat ttttcatctg tttcatcaaa aaagacaact tgaaaagctg | 600 |

-continued

```
ataagaaggc gggtttcaga aaacaaaagg cgatacacaa gggatggatt tgacctagac    660
ctcacttacg ttacagaacg tattattgct atgtcatttc catcttctgg aaggcagtct    720
ttctatagaa atccaatcaa ggaagttgtg cggtttctag ataagaaaca ccgaaaccac    780
tatcgagtct acaatctatg cagtgaaaga gcttacgatc ctaagcactt ccataatagg    840
gtcgttagaa tcatgattga tgatcataat gtccccactc tacatcagat ggtggttttc    900
accaaggaag taaatgagtg gatggctcaa gatcttgaaa acatcgtagc gattcactgt    960
aaaggaggca caggttatgt acgtgatcta aaaatccaaa tagaaatgga gaaaaggtt    1020 gtctttttcca ctatttcatt aggaaaatgt tcggtacttg ataacattac aacagacaaa   1080
atattaattg atgtattcga cggtccacct ctgtatgatg atgtgaaagt gcagttttc    1140 tattcgaatc ttcctacata ctatgacaat tgctcatttt acttctggtt gcacacatct   1200
tttattgaaa ataacaggct ttatctacca aaaaatgaat tggataatct acataaacaa   1260
aaagcacgga gaatttatcc atcagattt gccgtggaga tacttttttgg cgagaaaatg   1320 acttccagtg atgttgtagc tggatccgat taa                               1353
```

<210> SEQ ID NO 8
<211> LENGTH: 551
<212> TYPE: PRT
<213> ORGANISM: Homo sapiens

<400> SEQUENCE: 8

```
Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Gly Lys Leu Ile Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
```

```
                    245                 250                 255
Gln Ser Phe Tyr Arg Asn Pro Ile Lys Glu Val Val Arg Phe Leu Asp
            260                 265                 270
Lys Lys His Arg Asn His Tyr Arg Val Tyr Asn Leu Cys Ser Glu Arg
        275                 280                 285
Ala Tyr Asp Pro Lys His Phe His Asn Arg Val Val Arg Ile Met Ile
    290                 295                 300
Asp Asp His Asn Val Pro Thr Leu His Gln Met Val Val Phe Thr Lys
305                 310                 315                 320
Glu Val Asn Glu Trp Met Ala Gln Asp Leu Glu Asn Ile Val Ala Ile
                325                 330                 335
His Cys Lys Gly Gly Thr Asp Arg Thr Gly Thr Met Val Cys Ala Phe
            340                 345                 350
Leu Ile Ala Ser Glu Ile Cys Ser Thr Ala Lys Glu Ser Leu Tyr Tyr
        355                 360                 365
Phe Gly Glu Arg Arg Thr Asp Lys Thr His Ser Glu Lys Phe Gln Gly
    370                 375                 380
Val Glu Thr Pro Ser Gln Lys Arg Tyr Val Ala Tyr Phe Ala Gln Val
385                 390                 395                 400
Lys His Leu Tyr Asn Trp Asn Leu Pro Pro Arg Arg Ile Leu Phe Ile
                405                 410                 415
Lys His Phe Ile Ile Tyr Ser Ile Pro Arg Tyr Val Arg Asp Leu Lys
            420                 425                 430
Ile Gln Ile Glu Met Glu Lys Lys Val Val Phe Ser Thr Ile Ser Leu
        435                 440                 445
Gly Lys Cys Ser Val Leu Asp Asn Ile Thr Thr Asp Lys Ile Leu Ile
    450                 455                 460
Asp Val Phe Asp Gly Pro Pro Leu Tyr Asp Asp Val Lys Val Gln Phe
465                 470                 475                 480
Phe Tyr Ser Asn Leu Pro Thr Tyr Tyr Asp Asn Cys Ser Phe Tyr Phe
                485                 490                 495
Trp Leu His Thr Ser Phe Ile Glu Asn Asn Arg Leu Tyr Leu Pro Lys
            500                 505                 510
Asn Glu Leu Asp Asn Leu His Lys Gln Lys Ala Arg Arg Ile Tyr Pro
        515                 520                 525
Ser Asp Phe Ala Val Glu Ile Leu Phe Gly Lys Met Thr Ser Ser
    530                 535                 540
Asp Val Val Ala Gly Ser Asp
545                 550

<210> SEQ ID NO 9
<211> LENGTH: 533
<212> TYPE: PRT
<213> ORGANISM: Homo sapiens

<400> SEQUENCE: 9

Met Asn Glu Ser Pro Asp Pro Thr Asp Leu Ala Gly Val Ile Ile Glu
1               5                   10                  15
Leu Gly Pro Asn Asp Ser Pro Gln Thr Ser Glu Phe Lys Gly Ala Thr
            20                  25                  30
Glu Glu Ala Pro Ala Lys Glu Ser Val Leu Ala Arg Leu Ser Lys Phe
        35                  40                  45
Glu Val Glu Asp Ala Glu Asn Val Ala Ser Tyr Asp Ser Lys Ile Lys
    50                  55                  60
Lys Ile Val His Ser Ile Val Ser Ser Phe Ala Phe Gly Leu Phe Gly
```

-continued

```
                65                  70                  75                  80
Val Phe Leu Val Leu Leu Asp Val Thr Leu Ile Leu Ala Asp Leu Ile
                    85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Gln Lys Arg Tyr Val Ala Tyr Phe Ala Gln Val Lys His
    370                 375                 380

Leu Tyr Asn Trp Asn Leu Pro Pro Arg Arg Ile Leu Phe Ile Lys His
385                 390                 395                 400

Phe Ile Ile Tyr Ser Ile Pro Arg Tyr Val Arg Asp Leu Lys Ile Gln
                405                 410                 415

Ile Glu Met Glu Lys Lys Val Val Phe Ser Thr Ile Ser Leu Gly Lys
            420                 425                 430

Cys Ser Val Leu Asp Asn Ile Thr Thr Asp Lys Ile Leu Ile Asp Val
        435                 440                 445

Phe Asp Gly Pro Pro Leu Tyr Asp Asp Val Lys Val Gln Phe Phe Tyr
    450                 455                 460

Ser Asn Leu Pro Thr Tyr Tyr Asp Asn Cys Ser Phe Tyr Phe Trp Leu
465                 470                 475                 480

His Thr Ser Phe Ile Glu Asn Asn Arg Leu Tyr Leu Pro Lys Asn Glu
                485                 490                 495
```

Leu Asp Asn Leu His Lys Gln Lys Ala Arg Arg Ile Tyr Pro Ser Asp
            500                 505                 510

Phe Ala Val Glu Ile Leu Phe Gly Glu Lys Met Thr Ser Ser Asp Val
            515                 520                 525

Val Ala Gly Ser Asp
            530

<210> SEQ ID NO 10
<211> LENGTH: 569
<212> TYPE: PRT
<213> ORGANISM: Homo sapiens

<400> SEQUENCE: 10

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Leu Leu Arg Ile Phe His Leu
        195                 200                 205

Phe His Gln Lys Arg Gly Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Met Tyr
        275                 280                 285

Ile Thr Leu Tyr Cys Ala Thr Val Asp Arg Lys Gln Ile Thr Ala Arg
    290                 295                 300

Glu Arg Ala Tyr Asp Pro Lys His Phe His Asn Arg Val Val Arg Ile
305                 310                 315                 320

Met Ile Asp Asp His Asn Val Pro Thr Leu His Gln Met Val Val Phe
                325                 330                 335

```
Thr Lys Glu Val Asn Glu Trp Met Ala Gln Asp Leu Glu Asn Ile Val
            340                 345                 350

Ala Ile His Cys Lys Gly Gly Thr Asp Arg Thr Gly Thr Met Val Cys
            355                 360                 365

Ala Phe Leu Ile Ala Ser Glu Ile Cys Ser Thr Ala Lys Glu Ser Leu
            370                 375                 380

Tyr Tyr Phe Gly Glu Arg Arg Thr Asp Lys Thr His Ser Glu Lys Phe
385                 390                 395                 400

Gln Gly Val Glu Thr Pro Ser Gln Lys Arg Tyr Val Ala Tyr Phe Ala
                405                 410                 415

Gln Val Lys His Leu Tyr Asn Trp Asn Leu Pro Pro Arg Ile Leu
                420                 425                 430

Phe Ile Lys His Phe Ile Ile Tyr Ser Ile Pro Arg Tyr Val Arg Asp
            435                 440                 445

Leu Lys Ile Gln Ile Glu Met Glu Lys Lys Val Val Phe Ser Thr Ile
            450                 455                 460

Ser Leu Gly Lys Cys Ser Val Leu Asp Asn Ile Thr Thr Asp Lys Ile
465                 470                 475                 480

Leu Ile Asp Val Phe Asp Gly Pro Pro Leu Tyr Asp Val Lys Val
                485                 490                 495

Gln Phe Phe Tyr Ser Asn Leu Pro Thr Tyr Tyr Asp Asn Cys Ser Phe
                500                 505                 510

Tyr Phe Trp Leu His Thr Ser Phe Ile Glu Asn Asn Arg Leu Tyr Leu
            515                 520                 525

Pro Lys Asn Glu Leu Asp Asn Leu His Lys Gln Lys Ala Arg Arg Ile
530                 535                 540

Tyr Pro Ser Asp Phe Ala Val Glu Ile Leu Phe Gly Glu Lys Met Thr
545                 550                 555                 560

Ser Ser Asp Val Val Ala Gly Ser Asp
                565

<210> SEQ ID NO 11
<211> LENGTH: 395
<212> TYPE: PRT
<213> ORGANISM: Homo sapiens

<400> SEQUENCE: 11

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Pro His Thr Ser Glu Phe Lys Gly
            35                  40                  45

Ala Ala Arg Val Ser Pro Ile Ser Glu Ser Val Leu Ala Arg Leu Ser
        50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
                100                 105                 110

Leu Ile Phe Thr Asp Ser Lys Leu Tyr Ile Pro Leu Glu Tyr Arg Ser
            115                 120                 125

Ile Ser Leu Ala Ile Ala Leu Phe Phe Leu Met Asp Val Leu Leu Arg
        130                 135                 140
```

```
Val Phe Val Glu Arg Arg Gln Gln Tyr Phe Ser Asp Leu Phe Asn Ile
145                 150                 155                 160

Leu Asp Thr Ala Ile Val Ile Leu Leu Leu Val Asp Val Val Tyr
            165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
            195                 200                 205

Phe His Gln Lys Arg Gln Leu Glu Lys Leu Ile Arg Arg Val Ser
210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
                260                 265                 270

Lys Lys His Arg Asn His Tyr Arg Val Tyr Asn Leu Cys Ser Glu Arg
            275                 280                 285

Ala Tyr Asp Pro Lys His Phe His Asn Arg Val Arg Ile Met Ile
290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
            355                 360                 365

Phe Gly Glu Arg Arg Thr Asp Lys Thr His Ser Glu Lys Phe Gln Gly
            370                 375                 380

Val Glu Thr Pro Ser Gln Val Met Tyr Val Ile
385                 390                 395

<210> SEQ ID NO 12
<211> LENGTH: 468
<212> TYPE: PRT
<213> ORGANISM: Homo sapiens

<400> SEQUENCE: 12

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Pro His Thr Ser Glu Phe Lys Gly
            35                  40                  45

Ala Ala Arg Val Ser Pro Ile Ser Glu Ser Val Leu Ala Arg Leu Ser
            50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
                100                 105                 110

Leu Ile Phe Thr Asp Ser Lys Leu Tyr Ile Pro Leu Glu Tyr Arg Ser
            115                 120                 125
```

```
Ile Ser Leu Ala Ile Ala Leu Phe Phe Leu Met Asp Val Leu Leu Arg
    130                 135                 140
Val Phe Val Glu Arg Arg Gln Gln Tyr Phe Ser Asp Leu Phe Asn Ile
145                 150                 155                 160
Leu Asp Thr Ala Ile Ile Val Ile Leu Leu Val Asp Val Val Tyr
                165                 170                 175
Ile Phe Phe Asp Ile Lys Leu Leu Arg Asn Ile Pro Arg Trp Thr His
                180                 185                 190
Leu Leu Arg Leu Leu Arg Leu Ile Ile Leu Leu Arg Ile Phe His Leu
            195                 200                 205
Phe His Gln Lys Arg Gln Leu Glu Lys Leu Ile Arg Arg Val Ser
    210                 215                 220
Glu Asn Lys Arg Arg Tyr Thr Arg Asp Gly Phe Asp Leu Asp Leu Thr
225                 230                 235                 240
Tyr Val Thr Glu Arg Ile Ile Ala Met Ser Phe Pro Ser Ser Gly Arg
                245                 250                 255
Gln Ser Phe Tyr Arg Asn Pro Ile Lys Glu Val Val Arg Phe Leu Asp
                260                 265                 270
Lys Lys His Arg Asn His Tyr Arg Val Tyr Asn Leu Cys Ser Glu Arg
            275                 280                 285
Ala Tyr Asp Pro Lys His Phe His Asn Arg Val Arg Ile Met Ile
    290                 295                 300
Asp Asp His Asn Val Pro Thr Leu His Gln Met Val Val Phe Thr Lys
305                 310                 315                 320
Glu Val Asn Glu Trp Met Ala Gln Asp Leu Glu Asn Ile Val Ala Ile
                325                 330                 335
His Cys Lys Gly Gly Thr Gly Tyr Val Arg Asp Leu Lys Ile Gln Ile
                340                 345                 350
Glu Met Glu Lys Lys Val Val Phe Ser Thr Ile Ser Leu Gly Lys Cys
            355                 360                 365
Ser Val Leu Asp Asn Ile Thr Thr Asp Lys Ile Leu Ile Asp Val Phe
    370                 375                 380
Asp Gly Pro Pro Leu Tyr Asp Asp Val Lys Val Gln Phe Phe Tyr Ser
385                 390                 395                 400
Asn Leu Pro Thr Tyr Tyr Asp Asn Cys Ser Phe Tyr Phe Trp Leu His
                405                 410                 415
Thr Ser Phe Ile Glu Asn Asn Arg Leu Tyr Leu Pro Lys Asn Glu Leu
                420                 425                 430
Asp Asn Leu His Lys Gln Lys Ala Arg Arg Ile Tyr Pro Ser Asp Phe
            435                 440                 445
Ala Val Glu Ile Leu Phe Gly Glu Lys Met Thr Ser Ser Asp Val Val
    450                 455                 460
Ala Gly Ser Asp
465

<210> SEQ ID NO 13
<211> LENGTH: 470
<212> TYPE: PRT
<213> ORGANISM: Homo sapiens

<400> SEQUENCE: 13

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30
```

```
Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
 50                  55                  60

Lys Ile Val His Ser Ile Val Ser Ser Phe Ala Phe Gly Leu Phe Gly
 65                  70                  75                  80

Val Phe Leu Val Leu Leu Asp Val Thr Leu Ile Leu Ala Asp Leu Ile
                 85                  90                  95

Phe Thr Asp Ser Lys Leu Tyr Ile Pro Leu Glu Tyr Arg Ser Ile Ser
                100                 105                 110

Leu Ala Ile Ala Leu Phe Phe Leu Met Asp Val Leu Leu Arg Val Phe
            115                 120                 125

Val Glu Arg Arg Gln Gln Tyr Phe Ser Asp Leu Phe Asn Ile Leu Asp
130                 135                 140

Thr Ala Ile Ile Val Ile Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Val Ser Glu Asn
        195                 200                 205

Lys Arg Arg Tyr Thr Arg Asp Gly Phe Asp Leu Asp Leu Thr Tyr Val
210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Val Leu Asp Asn Ile Thr Thr Lys Ile Leu Ile Asp
370                 375                 380

Val Phe Asp Gly Pro Pro Leu Tyr Asp Asp Val Lys Val Gln Phe Phe
385                 390                 395                 400

Tyr Ser Asn Leu Pro Thr Tyr Tyr Asp Asn Cys Ser Phe Tyr Phe Trp
                405                 410                 415

Leu His Thr Ser Phe Ile Glu Asn Asn Arg Leu Tyr Leu Pro Lys Asn
            420                 425                 430

Glu Leu Asp Asn Leu His Lys Gln Lys Ala Arg Arg Ile Tyr Pro Ser
        435                 440                 445

Asp Phe Ala Val Glu Ile Leu Phe Gly Glu Lys Met Thr Ser Ser Asp
450                 455                 460
```

-continued

Val Val Ala Gly Ser Asp
465             470

<210> SEQ ID NO 14
<211> LENGTH: 450
<212> TYPE: PRT
<213> ORGANISM: Homo sapiens

<400> SEQUENCE: 14

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Gly Tyr Val Arg Asp Leu Lys Ile Gln Ile Glu Met
                325                 330                 335

Glu Lys Lys Val Val Phe Ser Thr Ile Ser Leu Gly Lys Cys Ser Val
            340                 345                 350

Leu Asp Asn Ile Thr Thr Asp Lys Ile Leu Ile Asp Val Phe Asp Gly
        355                 360                 365

```
Pro Pro Leu Tyr Asp Asp Val Lys Val Gln Phe Phe Tyr Ser Asn Leu
    370                 375                 380
Pro Thr Tyr Tyr Asp Asn Cys Ser Phe Tyr Phe Trp Leu His Thr Ser
385                 390                 395                 400
Phe Ile Glu Asn Asn Arg Leu Tyr Leu Pro Lys Asn Glu Leu Asp Asn
                405                 410                 415
Leu His Lys Gln Lys Ala Arg Arg Ile Tyr Pro Ser Asp Phe Ala Val
            420                 425                 430
Glu Ile Leu Phe Gly Glu Lys Met Thr Ser Ser Asp Val Val Ala Gly
        435                 440                 445
Ser Asp
    450

<210> SEQ ID NO 15
<211> LENGTH: 21
<212> TYPE: DNA
<213> ORGANISM: Artificial sequence
<220> FEATURE:
<223> OTHER INFORMATION: Target sequence

<400> SEQUENCE: 15
tcggtacttg ataacattac a                                         21

<210> SEQ ID NO 16
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 16
gguacuugau aacauuacat t                                         21

<210> SEQ ID NO 17
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 17
uguaauguua ucaaguaccg a                                         21

<210> SEQ ID NO 18
<211> LENGTH: 21
<212> TYPE: DNA
<213> ORGANISM: Artificial sequence
<220> FEATURE:
<223> OTHER INFORMATION: Target sequence

<400> SEQUENCE: 18
cagacttgtg ttattctagc a                                         21

<210> SEQ ID NO 19
<211> LENGTH: 21
<212> TYPE: DNA
<213> ORGANISM: Artificial sequence
```

```
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 19
gacuuguguu auucuagcat t                                              21

<210> SEQ ID NO 20
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 20
ugcuagaaua acacaaguct g                                              21

<210> SEQ ID NO 21
<211> LENGTH: 21
<212> TYPE: DNA
<213> ORGANISM: Artificial sequence
<220> FEATURE:
<223> OTHER INFORMATION: Target sequence

<400> SEQUENCE: 21
ctgaaatatg ttcaactgca a                                              21

<210> SEQ ID NO 22
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 22
gaaauauguu caacugcaat t                                              21

<210> SEQ ID NO 23
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 23
uugcaguuga acauauuuca g                                              21

<210> SEQ ID NO 24
<211> LENGTH: 21
<212> TYPE: DNA
<213> ORGANISM: Artificial sequence
<220> FEATURE:
<223> OTHER INFORMATION: Target sequence

<400> SEQUENCE: 24
```

```
cagattggca accaagacta a                                              21

<210> SEQ ID NO 25
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 25
gauuggcaac caagacuaat t                                              21

<210> SEQ ID NO 26
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 26
uuagucuugg uugccaauct g                                              21

<210> SEQ ID NO 27
<211> LENGTH: 21
<212> TYPE: DNA
<213> ORGANISM: Artificial sequence
<220> FEATURE:
<223> OTHER INFORMATION: Target sequence

<400> SEQUENCE: 27
aaccctgcca catgttcata t                                              21

<210> SEQ ID NO 28
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 28
cccugccaca uguucauaut t                                              21

<210> SEQ ID NO 29
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 29
auaugaacau guggcagggt t                                              21
```

```
<210> SEQ ID NO 30
<211> LENGTH: 21
<212> TYPE: DNA
<213> ORGANISM: Artificial sequence
<220> FEATURE:
<223> OTHER INFORMATION: Target sequence

<400> SEQUENCE: 30
aatgacagtc cacagacaag t                                              21

<210> SEQ ID NO 31
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 31
ugacagucca cagacaagut t                                              21

<210> SEQ ID NO 32
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 32
acuugucugu ggacugucat t                                              21

<210> SEQ ID NO 33
<211> LENGTH: 21
<212> TYPE: DNA
<213> ORGANISM: Artificial sequence
<220> FEATURE:
<223> OTHER INFORMATION: Target sequence

<400> SEQUENCE: 33
aagctgataa gaaggcgggt t                                              21

<210> SEQ ID NO 34
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 34
gcugauaaga aggcggguut t                                              21

<210> SEQ ID NO 35
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
```

```
<222> LOCATION: (1)..(19)
<223> OTHER INFORMATION: ribonucleotide bases

<400> SEQUENCE: 35
aacccgccuu cuuaucagct t                                              21

<210> SEQ ID NO 36
<211> LENGTH: 21
<212> TYPE: DNA
<213> ORGANISM: Artificial sequence
<220> FEATURE:
<223> OTHER INFORMATION: Oligonucleotide

<400> SEQUENCE: 36
tggatgtcac tctcatcctt g                                              21

<210> SEQ ID NO 37
<211> LENGTH: 21
<212> TYPE: DNA
<213> ORGANISM: Artificial sequence
<220> FEATURE:
<223> OTHER INFORMATION: Oligonucleotide

<400> SEQUENCE: 37
ccatagttcc tgttctatct g                                              21

<210> SEQ ID NO 38
<211> LENGTH: 21
<212> TYPE: DNA
<213> ORGANISM: Artificial sequence
<220> FEATURE:
<223> OTHER INFORMATION: Oligonucleotide

<400> SEQUENCE: 38
gagtctacaa tctatgcagt g                                              21

<210> SEQ ID NO 39
<211> LENGTH: 21
<212> TYPE: DNA
<213> ORGANISM: Artificial sequence
<220> FEATURE:
<223> OTHER INFORMATION: Oligonucleotide

<400> SEQUENCE: 39
cgatgctctt agctgagtgt c                                              21

<210> SEQ ID NO 40
<211> LENGTH: 21
<212> TYPE: DNA
<213> ORGANISM: Artificial sequence
<220> FEATURE:
<223> OTHER INFORMATION: Oligonucleotide

<400> SEQUENCE: 40
taaccagaca aatcgctcca c                                              21

<210> SEQ ID NO 41
<211> LENGTH: 46
<212> TYPE: DNA
<213> ORGANISM: Artificial sequence
<220> FEATURE:
<223> OTHER INFORMATION: Oligonucleotide

<400> SEQUENCE: 41
gagagaaagc ttccaccatg aatgaaagtc ctgatccgac tgacct                   46
```

-continued

```
<210> SEQ ID NO 42
<211> LENGTH: 44
<212> TYPE: DNA
<213> ORGANISM: Artificial sequence
<220> FEATURE:
<223> OTHER INFORMATION: Oligonucleotide

<400> SEQUENCE: 42
gagagaaagc ttgatcggat ccagctacaa catcactgga agtc          44

<210> SEQ ID NO 43
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 43
uaacuguaua aucgacuagt t                                   21

<210> SEQ ID NO 44
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 44
cuagucgauu auacaguuag a                                   21

<210> SEQ ID NO 45
<211> LENGTH: 21
<212> TYPE: DNA
<213> ORGANISM: Artificial sequence
<220> FEATURE:
<223> OTHER INFORMATION: Oligonucleotide

<400> SEQUENCE: 45
cagctgacta aacagaagca g                                   21

<210> SEQ ID NO 46
<211> LENGTH: 22
<212> TYPE: DNA
<213> ORGANISM: Artificial sequence
<220> FEATURE:
<223> OTHER INFORMATION: Oligonucleotide

<400> SEQUENCE: 46
gagttgaatg cagtcatcac ag                                  22
```

COMPOSITIONS AND METHODS FOR THERAPY AND DIAGNOSIS OF CANCER

Figure 1:
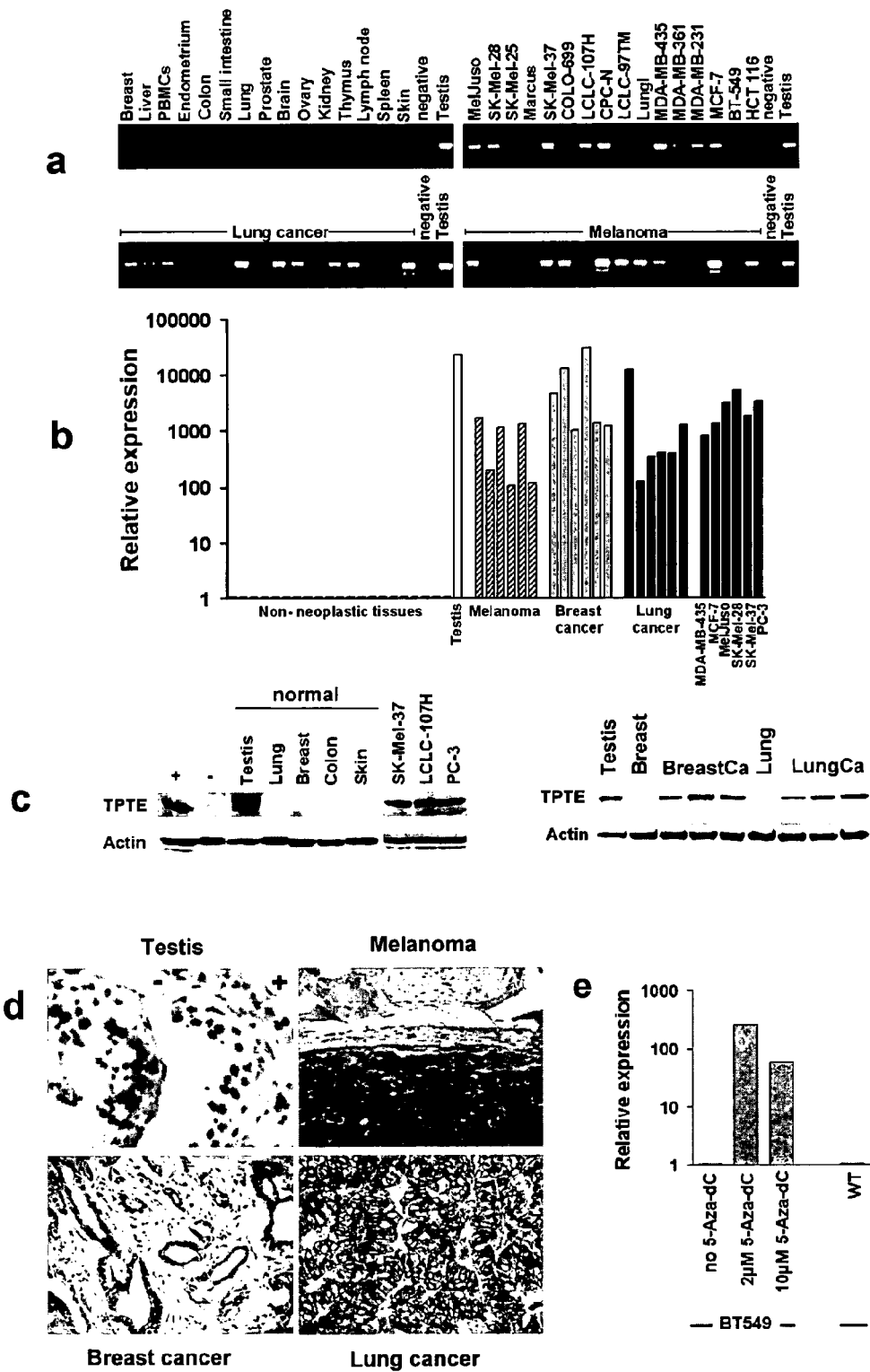

This application is a U.S. National-Stage Application of PCT/EP2006/011785, filed Dec. 7, 2006 and claiming priority benefit of European Patent Application Number 05 026 874.7, filed on Dec. 8, 2005, the contents of which are incorporated herein by reference in their entireties.

Despite interdisciplinary approaches and exhaustive use of classical therapeutic procedures, cancers are still among the leading causes of death.

Tumour cells biologically differ substantially from their nonmalignant cells of origin. These differences are due to genetic alterations acquired during tumour development and result, inter alia, also in the formation of qualitatively or quantitatively altered molecular structures in the cancer cells. Tumour-associated structures of this kind are, in particular, genetic products the expression of which is induced or enhanced during the course of malignant transformation.

RNA interference (hereinafter "RNAi") is a method of post-transcriptional gene regulation that is conserved throughout many eukaryotic organisms. RNAi is induced by short (i.e., <30 nucleotides) double stranded RNA ("dsRNA") molecules which are present in the cell (Fire A et al. (1998), Nature 391: 806-811). These short dsRNA molecules, called "short interfering RNA" or "siRNA" cause the destruction of messenger RNAs ("mRNAs") which share sequence homology with the siRNA to within one nucleotide resolution (Elbashir S M et al. (2001), Genes Dev, 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Elbashir S M et al. (2001) have shown that synthetic siRNA of 21 and 22 nucleotides in length, and which have short 3' overhangs, are able to induce RNAi of target mRNA in a *Drosophila* cell lysate. Cultured mammalian cells also exhibit RNAi degradation with synthetic siRNA (Elbashir S M et al. (2001), Nature, 411: 494-498), and RNAi degradation induced by synthetic siRNA has been shown in living mice (McCaffrey A P et al. (2002), Nature, 418: 38-39; Xia H et al. (2002), Nat. Biotech. 20: 1006-1010). The therapeutic potential of siRNA-induced RNAi degradation has been demonstrated in several recent in vitro studies, including the siRNA-directed inhibition of HIV-1 infection (Novina C D et al. (2002), Nat. Med. 8: 681-686) and reduction of neurotoxic polyglutamine disease protein expression (Xia H et al. (2002), supra).

RNA interference may be effected by introducing double-stranded RNA into cells as well as transfecting the cells with a plasmid carrying a hairpin-structured siRNA expressing cassette under the control of suitable promoters, such as the U6, H1 or cytomegalovirus ("CMV") promoter.

It was the object of the present invention to provide compositions and methods for a therapy, prophylaxis and diagnosis of cancers, in particular cancer metastases.

These objects are achieved by the subject matter of the claims.

The studies presented herein demonstrate that TPTE transcription is initiated during the course of malignant transformation by cancer-associated DNA hypomethylation. Furthermore, the studies presented herein indicate that TPTE promotes cancer progression and metastatic spread of cancer cells. In particular, TPTE is vital for efficient chemotaxis, a process which is involved in multiple aspects of cancer progression including cancer invasion and metastasis with impact on homing and metastatic destination of tumour cells. The findings presented herein have clinical implications for the prognostic classification and treatment of TPTE expressing tumours. TPTE expression in primary tumours is associated with a significantly higher rate of metastatic disease and TPTE can therefore serve as a prognostic marker. Using siRNA it was possible to inhibit expression of TPTE to less than 15% of baseline levels.

In a first aspect the present invention is directed to siRNA molecules which specifically target and cause RNAi-induced degradation of mRNA from TPTE genes, so that the protein product of the TPTE gene is not produced or is produced in reduced amounts. The siRNA compounds and compositions of the invention are useful for treating and/or preventing diseases which require inhibition of TPTE expression for their treatment and/or prevention, in particular cancer pathologies such as the metastasis of cancer.

The siRNA of the invention comprises short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired").

Specifically, the invention relates to a siRNA comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in TPTE mRNA. Preferably, the siRNA of the invention is isolated.

In one embodiment said TPTE mRNA comprises a nucleic acid sequence which is selected from the group consisting of (a) a nucleic acid sequence selected from the group consisting of SEQ ID NOs: 1, 2, 3, 4, 5, 6, and 7, a part or derivative thereof, (b) a nucleic acid sequence which hybridizes with the nucleic acid sequence of (a) under stringent conditions, (c) a nucleic acid sequence which is degenerate with respect to the nucleic acid of (a) or (b), (d) a nucleic acid sequence which is complementary to the nucleic acid sequence of (a), (b) or (c), and (e) a nucleic acid sequence which encodes an amino acid sequence selected from the group consisting of SEQ ID NOs: 8, 9, 10, 11, 12, 13, and 14, a part or derivative thereof.

In one embodiment, the siRNA molecule of the invention is assembled from two nucleic acid fragments wherein one fragment comprises the sense region and the second fragment comprises the antisense region of said siRNA molecule. In a further embodiment of the siRNA molecule of the invention the sense and antisense RNA strands forming the RNA duplex are covalently linked by a single-stranded hairpin.

The siRNA of the invention preferably further comprises non-nucleotide material. In a further embodiment of the siRNA of the invention the sense and antisense RNA strands are stabilized against nuclease degradation.

Preferably the siRNA of the invention further comprises a 3'-overhang preferably comprising from 1 to about 6 nucleotides, more preferably about 2 nucleotides.

In one embodiment of the siRNA of the invention the sense RNA strand comprises a first 3'-overhang, and the antisense RNA strand comprises a second 3'-overhang, wherein preferably the first and second 3'-overhangs independently comprise from 1 to about 6 nucleotides. More preferably the first 3'-overhang comprises a dinucleotide and the second 3'-overhang comprises a dinucleotide, preferably dideoxythymidylic acid or diuridylic acid.

In one embodiment of the siRNA of the invention the 3'-overhang is stabilized against nuclease degradation.

In particular embodiments of the siRNA of the invention the target sequence has a nucleic acid sequence selected from the group consisting of nucleotide positions 3-21 of SEQ ID NO: 15, nucleotide positions 3-21 of SEQ ID NO: 18, nucleotide positions 3-21 of SEQ ID NO: 21, nucleotide positions 3-21 of SEQ ID NO: 24, nucleotide positions 3-21 of SEQ ID NO: 27, nucleotide positions 3-21 of SEQ ID NO: 30, and nucleotide positions 3-21 of SEQ ID NO: 33. In further particular embodiments of the siRNA of the invention the sense RNA strand has the sequence of SEQ ID NO: 16 and the antisense RNA strand has the sequence of SEQ ID NO: 17, or sense RNA strand has the sequence of SEQ ID NO: 19 and the antisense RNA strand has the sequence of SEQ ID NO: 20, or the sense RNA strand has the sequence of SEQ ID NO: 22 and the antisense RNA strand has the sequence of SEQ ID NO: 23, or the sense RNA strand has the sequence of SEQ ID NO: 25 and the antisense RNA strand has the sequence of SEQ ID NO: 26, or the sense RNA strand has the sequence of SEQ ID NO: 28 and the antisense RNA strand has the sequence of SEQ ID NO: 29, or the sense RNA strand has the sequence of SEQ ID NO: 31 and the antisense RNA strand has the sequence of SEQ ID NO: 32, or the sense RNA strand has the sequence of SEQ ID NO: 34 and the antisense RNA strand has the sequence of SEQ ID NO: 35.

In a further aspect the present invention relates to an expression vector comprising nucleic acid sequences for expressing a sense RNA strand, an antisense RNA strand, or both of a siRNA according to the invention. Preferably the expression vector comprises a promoter functionally linked to the nucleic acid sequences for expressing a sense RNA strand, an antisense RNA strand, or both of a siRNA according to the invention, preferably an inducible or regulatable promoter.

In a further aspect the present invention relates to a recombinant viral vector comprising nucleic acid sequences for expressing a sense RNA strand, an antisense RNA strand, or both of a siRNA according to the invention. Preferably the recombinant viral vector comprises a promoter functionally linked to said nucleic acid sequences for expressing a sense RNA strand, an antisense RNA strand, or both of a siRNA according to the invention, preferably an inducible or regulatable promoter. In particular embodiments the recombinant viral vector of the invention is selected from the group consisting of an adenoviral vector, an adeno-associated viral vector, a lentiviral vector, a retroviral vector, and a herpes virus vector.

In a further aspect the invention relates to a pharmaceutical composition comprising a siRNA, an expression vector, and/or a recombinant viral vector of the invention. Preferably the pharmaceutical composition of the invention may be used for the treatment or prevention of cancer and/or cancer metastasis, wherein the cancer is preferably a lung tumour, a breast tumour, a prostate tumour, a melanoma, a colon tumour, a gastric tumour, a pancreatic tumour, an ENT tumour, a renal cell carcinoma or a cervical carcinoma, a colon carcinoma or a mammary carcinoma.

A pharmaceutical composition of the invention may comprise a pharmaceutically compatible carrier and/or an adjuvant.

In a further aspect the present invention relates to a method of inhibiting expression of TPTE, comprising administering to a subject an effective amount of a siRNA, an expression vector, a recombinant viral vector and/or a pharmaceutical composition of the invention, such that the TPTE mRNA is degraded.

In a further aspect the present invention relates to a method of treating cancer in a subject, comprising administering to a subject an effective amount of an siRNA, an expression vector, a recombinant viral vector and/or a pharmaceutical composition of the invention.

In a further aspect the present invention relates to a method of inhibiting cancer metastasis in a subject, comprising administering to a subject an effective amount of an siRNA, an expression vector, a recombinant viral vector and/or a pharmaceutical composition of the invention.

In the methods of the invention the cancer or cancer metastasis is preferably characterized by expression or abnormal expression of (i) a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) a protein or peptide encoded by the nucleic acid under (i).

Preferably the nucleic acid under (i) comprises a nucleic acid sequence encoding a protein or peptide comprising an amino acid sequence selected from the group consisting of SEQ ID NOs: 8, 9, 10, 11, 12, 13, and 14, a part or derivative thereof and/or the protein or peptide under (ii) comprises an amino acid sequence selected from the group consisting of SEQ ID NOs: 8, 9, 10, 11, 12, 13, and 14, a part or derivative thereof.

In the methods of the invention the siRNA, the expression vector, the recombinant viral vector and/or the pharmaceutical composition is preferably administered in combination with radiation therapy, chemotherapy or surgery, wherein the chemotherapeutic agent is preferably selected from the group consisting of cisplatin, carboplatin, cyclophosphamide, 5-fluorouracil, adriamycin, daunorubicin, and tamoxifen.

Preferably the subject for administration is a human being.

Preferably the effective amount of the siRNA administered is from about 1 nM to about 100 nM.

In one embodiment the siRNA is administered in conjunction with a delivery agent, wherein the delivery agent is preferably selected from the group consisting of lipofectin, lipofectamine, cellfectin, polycations, and liposomes. Preferably the liposome comprises a ligand which targets the liposome to cells expressing TPTE, wherein the ligand preferably comprises an antibody.

In one embodiment of the methods of the invention the siRNA is expressed from a recombinant plasmid or a recombinant viral vector, wherein the recombinant viral vector preferably comprises an adenoviral vector, an adeno-associated viral vector, a lentiviral vector, or a herpes virus vector.

In one embodiment the siRNA is administered by an enteral administration route, wherein the enteral administration route is preferably selected form the group consisting of oral, rectal, and intranasal.

In a further embodiment the siRNA is administered by a parenteral administration route, wherein the parenteral administration route is preferably selected from the group consisting of intravascular administration, peri- and intratissue administration, subcutaneous injection or deposition, and subcutaneous infusion. Preferably the intravascular administration is selected from the group consisting of intravenous bolus injection, intravenous infusion, intra-arterial bolus injection, intra-arterial infusion and catheter instillation into the vasculature and the peri- and intra-tissue administration is preferably selected from the group consisting of peritumoural injection, and intra-tumoural injection.

The present invention also includes methods which make possible to assess and/or prognose the metastatic behaviour of a cancer disease and/or the occurrence of a relapse of cancer. Preferably, the methods of the invention allow to discriminate malign from benign conditions. In particular embodiments, the methods of the invention make possible to assess and/or prognose the success of a cancer therapy which has been administered or will be administered. In particular, the methods of the invention make possible to assess and/or prognose the occurrence of a relapse of cancer following cancer therapy, e.g., by surgery, chemotherapy and/or radiation therapy.

In this aspect, the invention relates to a method of determining, i.e. diagnosing, monitoring, i.e. determining the regression, progression, course and/or onset of, and/or prognosing the metastatic behaviour of cancer and/or the presence of a relapse of cancer, which method comprises (i) detecting or determining the amount of a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) detecting or determining the amount of a protein or peptide encoded by the nucleic acid under (i) or of a part or derivative thereof, and/or (iii) detecting or determining the amount of an antibody specific for the protein or peptide or the part or derivative under (ii), and/or (iv) detecting or determining the amount of a T lymphocyte specific for the protein or peptide or the part or derivative under (ii), optionally in a complex with a MHC molecule, in a biological sample isolated from a patient.

Preferably the nucleic acid under (i) comprises a nucleic acid sequence encoding a protein or peptide comprising an amino acid sequence selected from the group consisting of SEQ ID NOs: 8, 9, 10, 11, 12, 13, and 14, a part or derivative thereof and/or the protein or peptide under (ii) preferably comprises an amino acid sequence selected from the group consisting of SEQ ID NOs: 8, 9, 10, 11, 12, 13, and 14, a part or derivative thereof.

In one embodiment the presence of the nucleic acid, of the protein or peptide or part or derivative, of the antibody or of the T lymphocyte and/or an amount of the nucleic acid, of the protein or peptide or part or derivative, of the antibody or of the T lymphocyte which is increased compared to the amount in a subject without said cancer, without a risk for said cancer, without metastasis of said cancer, without a risk for metastasis of said cancer, without a relapse of said cancer, and/or without a risk for a relapse of said cancer is indicative for a metastatic behaviour of said cancer or a potential for a metastatic behaviour of said cancer and/or for a relapse of said cancer or a potential for a relapse of said cancer.

In a further preferred embodiment the detection or determination of the amount comprises (i) contacting the biological sample with an agent which binds to said nucleic acid, to said protein or peptide or part or derivative, to said antibody or to said T lymphocyte, and (ii) detecting the formation of or determining the amount of a complex between said agent and said nucleic acid, said protein or peptide or part or derivative, said antibody or said T lymphocyte.

In particular embodiments of the method of the invention, the patient has cancer, is suspected of having cancer or developing cancer, or has a risk for developing cancer. In further embodiments of the method of the invention, the patient has a cancer metastasis, is suspected of having a cancer metastasis or developing a cancer metastasis, or has a risk for developing a cancer metastasis. In particular embodiments of the method of the invention, the patient has already been subjected to cancer therapy such as by tumour resection, radiation therapy and/or chemotherapy, or it is intended to subject the patient to such therapy.

Means for accomplishing said detection and/or determination of the amount are described herein and will be apparent to the skilled person.

In a further embodiment, the biological sample isolated from the patient is compared to a comparable normal biological sample, e.g. a sample isolated from a healthy individual.

The methods of diagnosing, monitoring, and/or prognosing the metastatic behaviour of cancer and/or the presence of a relapse of cancer according to the invention may also involve the determination of methylation patterns and/or the degree of methylation with a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or with a nucleic acid comprising a nucleic acid sequence encoding a protein or peptide comprising an amino acid sequence selected from the group consisting of SEQ ID NOs: 8, 9, 10, 11, 12, 13, and 14, a part or derivative thereof, preferably within the non-coding region thereof and more preferably within the promoter region thereof.

A degree of methylation which is lower compared to a control, e.g. a subject without said cancer, without a risk for said cancer, without metastasis of said cancer, without a risk for metastasis of said cancer, without a relapse of said cancer, and/or without a risk for a relapse of said cancer, or no methylation preferably is indicative for a metastatic behaviour of said cancer or a potential for a metastatic behaviour of said cancer and/or for a relapse of said cancer or a potential for a relapse of said cancer.

The determination of methylation patterns and/or the degree of methylation can be performed, for example, by using methods on the basis of PCR, with the aid of restriction enzymes or by sequencing. In one preferred embodiment, genomic DNA is selectively amplified following treatment with a bisulfite containing reagent. The oligonucleotides used in such amplification preferably have a sequence binding to the nucleic acid treated with the bisulfite containing reagent and preferably are completely complementary thereto. Preferably the oligonucleotides are adapted to a different degree of methylation of the nucleic acid and bring about amplification products which can be differentiated. A test suitable for this can be as follows: (1) extraction of DNA from tissue samples of patients, for example using paraffin embedded material, (2) treatment of the DNA with bisulfite containing reagents (e.g. as described in Clark S. J. et al., Nucleic Acids Res. 22 (15):2990-7, 1994), (3) amplification of DNA by means of PCR and (4) analysis of the amount of sequence specific amplification products (e.g. by means of quantitative PCR, hybridization techniques such as microarray methods).

The methods of diagnosing, monitoring, and/or prognosing the metastatic behaviour of cancer and/or the presence of a relapse of cancer according to the invention preferably allow the prognosis of a worsened course of a disease, whereby among other things planning of a more aggressive therapy is made possible. These prognostic methods also allow to delimit still benign alterations, e.g. hyperplasias, from tumour precursors which are already to be appraised as unfavourable and to anticipate therefore a cancer disposition already before an invasive tumour has formed.

According to the invention, detection of a nucleic acid or determining the amount of a nucleic acid may be carried out using a oligo- or polynucleotide probe which hybridizes specifically to said nucleic acid, or may be carried out by selective amplification of said nucleic acid, e.g. by means of PCR amplification. In one embodiment, the probe comprises a sequence of 6-50, in particular 10-30, 15-30 and 20-30, contiguous nucleotides of said nucleic acid.

According to the invention, detection of a protein or peptide or of a part or derivative thereof or determining the amount of a protein or peptide or of a part or derivative thereof may be carried out using an antibody binding specifically to said protein or peptide or part or derivative thereof. In particular embodiments, the protein or peptide or part or derivative thereof which is to be detected or the amount of which is to be determined in the methods of the present invention is present in a complex with an MHC molecule.

According to the invention, detection of an antibody or determining the amount of an antibody may be carried out using a protein or peptide binding specifically to said antibody.

According to the invention, detection of a T lymphocyte or determining the amount of a T lymphocyte may be carried out using a cell presenting a complex between a protein or peptide and an MHC molecule for which the T lymphocyte is specific, wherein the cell is preferably an antigen-presenting cell. Detection of or determining the amount of a T lymphocyte may also be carried out by detecting its proliferation, cytokine production, and/or cytotoxic activity which may be triggered by specific stimulation with a complex between a protein or peptide and an MHC molecule for which the T lymphocyte is specific. Detection of or determining the amount of a T lymphocyte may also be carried out with aid of a recombinant MHC molecule or a complex of two or more MHC molecules loaded with one or more proteins or peptides.

An agent which is used for detection or determining the amount in the methods of the invention such as an oligo- or polynucleotide probe, an antibody, a protein or peptide or a cell is preferably labeled in a detectable manner, in particular by a detectable marker such as a radioactive marker, fluorescence marker or an enzymic marker.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

DETAILED DESCRIPTION OF THE INVENTION

The term "TPTE" relates to "transmembrane phosphatase with tensin homology" and includes any variants, in particular splice variant, conformations, isoforms and species homologs of TPTE which are naturally expressed by cells or are expressed by cells transfected with the TPTE gene. Preferably, a "nucleic acid of TPTE", a "nucleic acid encoding TPTE" or "TPTE gene" relates to a nucleic acid selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). Preferably, "TPTE" protein or simply "TPTE" comprises an amino acid sequence encoded by the afore mentioned nucleic acid, preferably an amino acid sequence selected from the group consisting of SEQ ID NOs: 8, 9, 10, 11, 12, 13, and 14, a part or derivative thereof. One skilled in the art would understand that the cDNA sequence of TPTE as described above would be equivalent to TPTE mRNA, and can be used for the same purpose herein; i.e., the generation of siRNA for inhibiting expression of TPTE.

The term "TPTE" also includes posttranslationally modified variants, isoforms and species homologs of human TPTE which are naturally expressed by cells or are expressed by cells transfected with the TPTE gene.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The term "nucleic acid" according to the invention also includes "derivatives" of a nucleic acid. "Derivative" of a nucleic acid means according to the invention that single or multiple, such as at least 2, at least 4, or at least 6 and preferably up to 3, up to 4, up to 5, up to 6, up to 10, up to 15, or up to 20 nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the terms "complementarity" or "complementary" means that a nucleic acid can form hydrogen bond(s) with another nucleic acid sequence by either traditional Watson-Crick or other non-traditional types of interaction. In reference to the nucleic molecules of the present invention, the binding free energy for a nucleic acid molecule with its complementary sequence is sufficient to allow the relevant function of the nucleic acid to proceed, e.g., RNAi activity. For example, the degree of complementarity between the sense and antisense strand of the siRNA construct can be the same or different from the degree of complementarity between the antisense strand of the siRNA and the target RNA sequence. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

Preferably, a nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

According to the invention, complementary nucleic acids preferably have at least 50%, at least 60%, at least 70%, at least 80%, at least 90% and preferably at least 95%, at least 98% or at least 99%, identical nucleotides.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

As used herein, a nucleic acid sequence "substantially identical" to a target sequence, e.g., a target sequence contained within a target mRNA, is a nucleic acid sequence which is identical to the target sequence, or which differs from the target sequence by one or more nucleotides. Sense strands of siRNAs of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand which differs from a target sequence by one, two or three or more nucleotides, as long as RNAi-mediated degradation of the target mRNA is induced by the siRNA.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, and CMV promoter.

According to the invention, the term "expression" is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

In those cases of the invention in which a MHC molecule presents a protein or peptide, an expression vector may also comprise a nucleic acid sequence coding for said MHC molecule. The nucleic acid sequence coding for the MHC molecule may be present on the same expression vector as the nucleic acid coding for the protein or peptide, or both nucleic acids may be present on different expression vectors. In the latter case, the two expression vectors may be cotransfected into a cell. If a host cell expresses neither the protein or peptide nor the MHC molecule, both nucleic acids coding therefor may be transfected into the cell either on the same expression vector or on different expression vectors. If the cell already expresses the MHC molecule, only the nucleic acid sequence coding for the protein or peptide can be transfected into the cell.

Amplification of a nucleic acid can be done using a pair of amplification primers, i.e. oligonucleotides, which hybridize to the nucleic acid. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid to be amplified, and the other primer will hybridize to the complementary strand in an arrangement which allows amplification of the nucleic acid.

According to the invention an oligonucleotide may be an oligoribonucleotide, oligodeoxyribonucleotide, modified oligoribonucleotide or modified oligo-deoxyribonucleotide.

In one embodiment, an oligonucleotide consists of ribonucleotides, deoxyribonucleotides or a combination thereof, with the 5'-end of one nucleotide and the 3'-end of another nucleotide being linked to one another by a phosphodiester bond. These oligonucleotides may be synthesized in the conventional manner or produced recombinantly.

In preferred embodiments, an oligonucleotide is a "modified" oligonucleotide. Here, the oligonucleotide may be modified in very different ways, without impairing its ability to bind its target, in order to increase, for example, its stability. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having one or more covalently modified bases and/or one or more covalently modified sugars. "Modified oligonucleotides" comprise, for example, oligonucleotides with sugar residues which are covalently bound to low molecular weight organic groups other than a hydroxyl group at the 3'-position and a phosphate group at the 5'-position. Modified oligonucleotides may comprise, for example, a 2'-O-alkylated ribose residue or another sugar instead of ribose, such as arabinose.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA of the invention can also comprise a 3'-overhang. As used herein, a "3'-overhang" refers to at least one unpaired nucleotide extending from the 3'-end of an RNA strand.

Thus in one embodiment, the siRNA of the invention comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the present siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the present siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation, in particular human TPTE mRNA, mutant or alternative splice forms of human TPTE mRNA, or mRNA from cognate TPTE genes. The human TPTE mRNA is given herein as the cDNA equivalent. One skilled in the art would understand that the cDNA sequence is equivalent to the mRNA sequence, and can be used for the same purpose herein, i.e., the generation of siRNA for inhibiting expression of TPTE.

As used herein, a gene or mRNA which is "cognate" to human TPTE is a gene or mRNA from another mammalian species which is homologous to human TPTE.

The mRNA transcribed from the human TPTE gene can be analyzed for alternative splice forms using techniques well-known in the art. Such techniques include reverse transcription-polymerase chain reaction (RT-PCR), northern blotting and in-situ hybridization.

A technique called "RNAse protection" can also be used to identify alternatively spliced TPTE mRNAs. RNAse protection involves transcription of a gene sequence into synthetic RNA, which is hybridized to RNA derived from other cells; for example, cells which are induced to express TPTE. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced TPTE mRNAs. In RT-PCR, mRNA from cells known to express TPTE is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The mRNA produced from mutant TPTE genes can also be readily identified with the techniques described above for identifying TPTE alternative splice forms. As used herein, "mutant" TPTE genes or mRNA include human TPTE genes or mRNA which differ in sequence from the TPTE sequences set forth herein. Thus, allelic forms of the TPTE gene, and the mRNA produced from them, are considered "mutants" for purposes of this invention.

It is understood that human TPTE mRNA may contain target sequences in common with its respective alternative splice forms, cognates or mutants. A single siRNA comprising such a common targeting sequence can therefore induce RNAi-mediated degradation of those different mRNAs which contain the common targeting sequence.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon. For example, a suitable target sequence in the TPTE cDNA sequence is selected from the following group of target sequences:

```
(i)     TCGGTACTTGATAACATTACA   (SEQ ID NO: 15)

(ii)    CAGACTTGTGTTATTCTAGCA   (SEQ ID NO: 18)

(iii)   CTGAAATATGTTCAACTGCAA   (SEQ ID NO: 21)

(iv)    CAGATTGGCAACCAAGACTAA   (SEQ ID NO: 24)

(v)     AACCCTGCCACATGTTCATAT   (SEQ ID NO: 27)

(vi)    AATGACAGTCCACAGACAAGT   (SEQ ID NO: 30)

(vii)   AAGCTGATAAGAAGGCGGGTT   (SEQ ID NO: 33)
```

A preferred siRNA of the invention targeting the sequence (i), and which has 3'-overhangs on each strand (overhangs shown in bold), is:

```
    gguacuugauaacauuacaTT    (SEQ ID NO: 16)
AGccaugaacuauuguaaugu        (SEQ ID NO: 17)
```

A preferred siRNA of the invention targeting the sequence (ii), and which has 3'-overhangs on each strand (overhangs shown in bold), is:

```
    gacuuguguuauucuagcaTT    (SEQ ID NO: 19)
GTcugaacacaauaagaucgu        (SEQ ID NO: 20)
```

A preferred siRNA of the invention targeting the sequence (iii), and which has 3'-overhangs on each strand (overhangs shown in bold), is:

```
    gaaauauguucaacugcaaTT    (SEQ ID NO: 22)
GAcuuuauacaaguugacguu        (SEQ ID NO: 23)
```

A preferred siRNA of the invention targeting the sequence (iv), and which has 3'-overhangs on each strand (overhangs shown in bold), is:

```
    gauuggcaaccaagacuaaTT    (SEQ ID NO: 25)
GTcuaaccguugguucugauu        (SEQ ID NO: 26)
```

A preferred siRNA of the invention targeting the sequence (v), and which has 3'-overhangs on each strand (overhangs shown in bold), is:

```
    cccugccacauguucauauTT    (SEQ ID NO: 28)
TTgggacgguguacaaguaua        (SEQ ID NO: 29)
```

A preferred siRNA of the invention targeting the sequence (vi), and which has 3'-overhangs on each strand (overhangs shown in bold), is:

```
    ugacaguccacagacaaguTT    (SEQ ID NO: 31)
TTacugucaggugucuguuca        (SEQ ID NO: 32)
```

A preferred siRNA of the invention targeting the sequence (vii), and which has 3'-overhangs on each strand (overhangs shown in bold), is:

```
    gcugauaagaaggcggguuTT    (SEQ ID NO: 34)
TTcgacuauucuuccgcccaa        (SEQ ID NO: 35)
```

In the above list, all deoxyribonucleotides in a nucleic acid sequence are represented by capital letters (e.g., deoxythymi-dine is "T"), and ribonucleotides in a nucleic acid sequence are represented by lower case letters (e.g., uridine is "u").

It is understood that the target sequences given herein are with reference to the human TPTE cDNA, and thus these sequences contain deoxythymidines represented by "T". One skilled in the art would understand that, in the actual target sequence of the TPTE mRNA, the deoxythymidines would be replaced by uridines ("u"). Likewise, a target sequence contained within an siRNA of the invention would also contain uridines in place of deoxythymidines.

The siRNA of the invention can be obtained using a number of techniques known to those of skill in the art. For example, the siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions.

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA of the invention to cells in vivo is discussed in more detail below. siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art.

The siRNA of the invention can also be expressed from recombinant viral vectors intracellularly in vivo. The recombinant viral vectors comprise sequences encoding the siRNA of the invention and any suitable promoter for expressing the siRNA sequences. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below. siRNA of the invention can be expressed from a recombinant viral vector either as two separate, complementary RNA molecules, or as a single RNA molecule with two complementary regions.

According to the invention the term "peptide" refers to substances comprising two or more, preferably 3 or more, preferably 4 or more, preferably 6 or more, preferably 8 or more, preferably 10 or more, preferably 13 or more, preferably 16 more, preferably 20 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used in this application interchangeably.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay. Proteins and peptides described according to the invention may be isolated from biological samples such as tissue or cell homogenates and may also be expressed recombinantly in a multiplicity of pro- or eukaryotic expression systems.

For the purposes of the present invention, "derivatives" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:
1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "derivatives" of proteins and peptides also comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides which do not only contain amino acid constituents but also non-amino acid constituents such as sugar and phosphate structures and extends also to substances containing bonds such ester, thioether and disulfide bonds.

According to the invention, a part or fragment of a protein or peptide preferably has a functional property of the protein or peptide from which it has been derived. Such functional properties comprise the interaction with antibodies, and the interaction with other peptides or proteins. A particular property is the ability to form a complex with MHC molecules and, where appropriate, generate an immune response, preferably by stimulating cytotoxic or T helper cells. A part or fragment of a protein or peptide preferably comprises a sequence of at least 6, in particular at least 8, at least 10, at least 12, at least 15, at least 20, at least 30 and preferably up to 8, in particular up to 10, up to 12, up to 15, up to 20, up to 30 or up to 50, consecutive amino acids of the protein or peptide.

A part or a fragment of a nucleic acid coding for a protein or peptide preferably relates to the part of the nucleic acid, which codes at least for the protein or peptide and/or for a part or a fragment of said protein or peptide, as defined above. A part or fragment of a nucleic acid coding for a protein or peptide is preferably that part of the nucleic acid corresponding to the open reading frame.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the invention, the term "antibody" also includes $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

Antibodies may also be coupled to specific diagnostic substances for displaying cells and tissues expressing particular proteins or peptides.

Diagnostic substances include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

The term "major histocompatibility complex" or "MHC" relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the invention an MHC molecule is an HLA molecule.

The term "patient" or "subject" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

"Abnormal expression" means according to the invention that expression is altered, preferably increased, compared to the state in a healthy individual. According to the invention the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the invention, the term "disease" refers to any pathological state, including, in particular, cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumours described above. According to the invention the term "cancer" also includes metastasis of cancer.

By "tumour" is meant an abnormal group of cells or tissue that grows by a rapid, uncontrolled cellular proliferation and continues to grow after the stimuli that initiated the new growth cease. Tumours show partial or complete lack of structural organization and functional coordination with the normal tissue, and usually form a distinct mass of tissue, which may be either benign or malignant.

Preferably, an siRNA of the invention is used to inhibit the growth or metastasis of solid tumours associated with cancers as described above.

By "metastasis" is meant the spread of cancer cells from its original site to another part of the body. The formation of metastasis is a very complex process and depends on detachment of malignant cells from the primary tumour, invasion of the extracellular matrix, penetration of the endothelial basement membranes to enter the body cavity and vessels, and then, after being transported by the blood, infiltration of target organs. Finally, the growth of a new tumour at the target site depends on angiogenesis. Tumour metastasis often occurs even after the removal of the primary tumour because tumour cells or components may remain and develop metastatic potential.

The term "relapse" relates to the return of signs and symptoms of a disease after a patient has enjoyed a remission, e.g. after therapy such as tumour resection, chemotherapy and/or radiation therapy. In particular, the term "relapse" relates to the reappearance of cancer after a disease-free period. For example, after treatment a patient with cancer went into remission with no sign or symptom of the tumour, remained in remission for some time, but then suffered a relapse and has to be treated once again for cancer.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids.

The terms "T cell" and "T lymphocyte" are used interchangeably herein and include T helper cells and cytolytic T cells which comprise cytotoxic T cells.

The pharmaceutical compositions and methods of treatment described according to the invention may also be used for immunization or vaccination to prevent a disease described herein.

In the present methods, the present siRNA can be administered to the subject either as naked siRNA, in conjunction with a delivery reagent, or as a recombinant plasmid or viral vector which expresses the siRNA. The invention also provides for administering nucleic acids in vivo by using target-controlled liposomes.

To deliver siRNA to cells in vivo, any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

Liposomes can aid in the delivery of the siRNA to a particular tissue, such as tumour tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

In particular embodiments, preference is given to directing nucleic acids to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively an antigen associated with tumour cells. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of TPTE protein in the cultured cells can be measured by ELISA or Western blot.

RNAi-mediated degradation of the target mRNA can be detected by measuring levels of the target mRNA or protein in the cells of a subject, using standard techniques for isolating and quantifying mRNA or protein as described above.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally.

Suitable techniques for delivering the siRNA of the invention to TPTE-expressing cells include administration of the siRNA to a subject by gene gun, electroporation, nanoparticles, micro-encapsulation, and the like, or by parenteral and enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoural and intra-tumoural injection); subcutaneous injection or deposition including subcutaneous infusion (such as by osmotic pumps); direct (e.g., topical) application at or near the site of the diseased area, for example by a catheter or other placement device (e.g., a suppository, or an implant comprising a porous, non-porous, or gelatinous material); and inhalation.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. As used herein, an "effective amount" of the siRNA is preferably an amount sufficient to cause RNAi-mediated degradation of the target mRNA in a subject.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

One skilled in the art can readily determine an effective amount of the siRNA of the invention to be administered to a given subject, by taking into account factors such as the size and weight of the subject; the extent of disease penetration; the age, health and sex of the subject; the route of administration; and whether the administration is regional or systemic. Generally, an effective amount of the siRNA of the invention comprises an intercellular concentration at the site where expression of TPTE is to be inhibited of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The siRNA of the invention can be administered to a subject in combination with another therapeutic method designed to treat the pathology. For example, the siRNA of the invention can be administered in combination with therapeutic methods currently employed for treating cancer or preventing tumour metastasis (e.g., radiation therapy, chemotherapy, and surgery). For treating tumours, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin ortamoxifen.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1 Selective Activation of TPTE Expression in Malignant Tissues and Cancer Cell Lines.

a, b, Analysis of TPTE mRNA expression by (a) conventional RT-PCR and (b) quantitative Real-Time RT-PCR in normal human tissues, tumour specimens and cancer cell lines. c, Western blot analysis of protein lysates obtained from normal tissues, constitutively TPTE-expressing cancer cell lines, and cancer tissues, respectively. Controls were NIH3T3 cells transfected with TPTE cDNA (+) and mock-transfected control cells (−). d, Immunohistochemical staining of testis and malignant tissues for TPTE. Blocking with the recombinant protein fragment used for immunization (+) as compared to the buffer control (−) confirmed specificity of the polyclonal antiserum pAK2091. e, Induction of TPTE mRNA expression in cells treated with the methylation inhibitor 5-Aza-2'-desoxycytidine and DNA methyltransferase knockout variants of HCT116 cells as shown by real time RT-PCR analysis.

Figure 2:
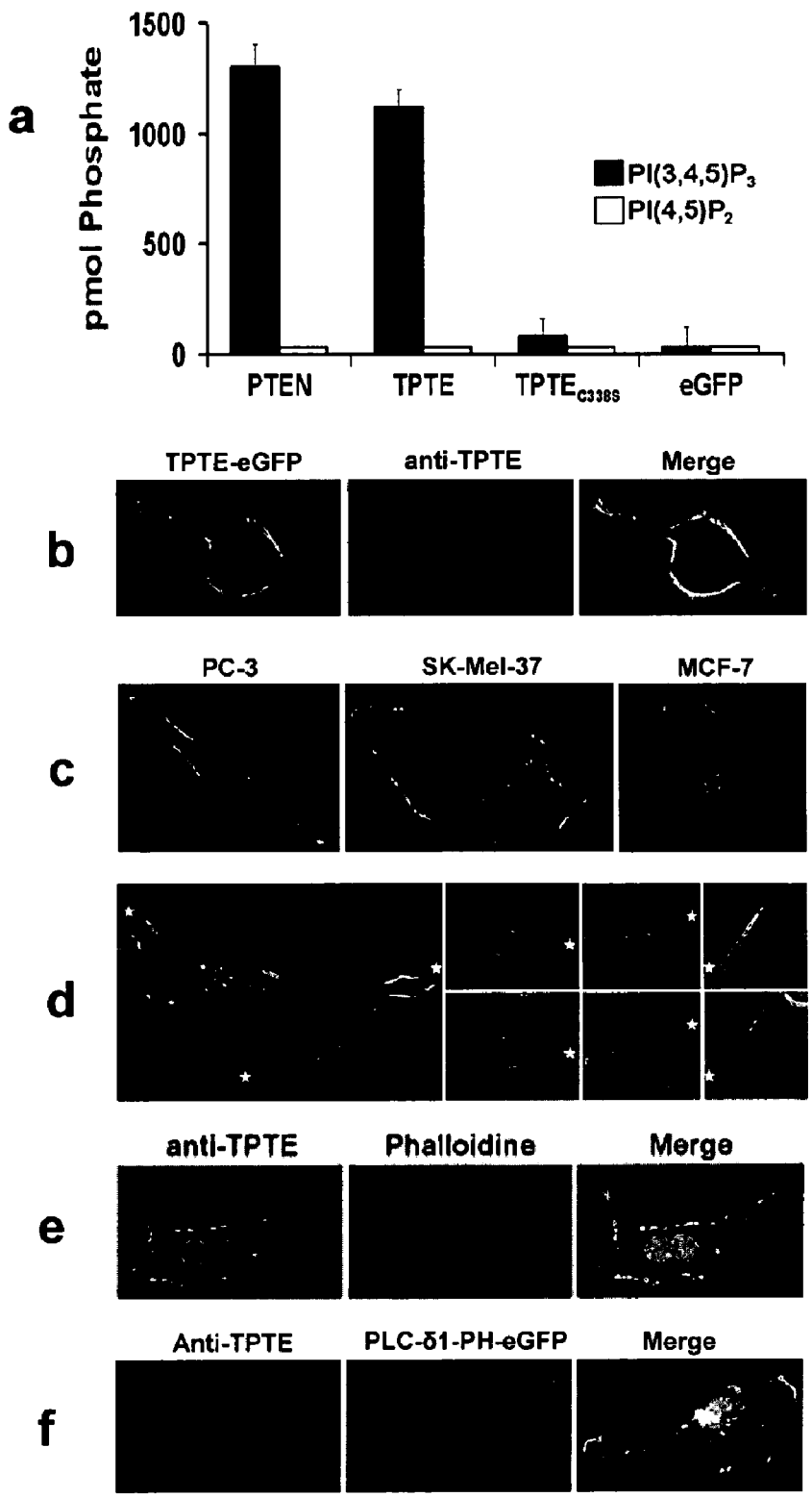

FIG. 2 TPTE is a Phosphoinositol 3'-Phosphatase Localised at the Plasma Membrane.

a, In vitro phosphatase assay with recombinant proteins using either $PI(3,4,5)P_3$ or $PI(4,5)P_2$ as substrates. b, Colocalisation of TPTE-eGFP fluorescence and pAK2091 staining for verification of the specificity of the polyclonal rabbit antiserum. c, Immunofluorescence analysis of cancer cell lines with constitutive expression of TPTE. d, Localisation of endogenous TPTE in filo- and pseudopodia of PC-3 prostate cancer cells; arrows, accumulation of TPTE at the lateral margins of cell protrusions; asteriks, tips of protrusions appear free of TPTE. e, f, Colocalisation of endogenously expressed TPTE in PC-3 cells with (e) F-Actin visualized by phalloidine staining and (f) $PIP_2$ visualised by PLC-d1-PH-eGFP.

Figure 3:
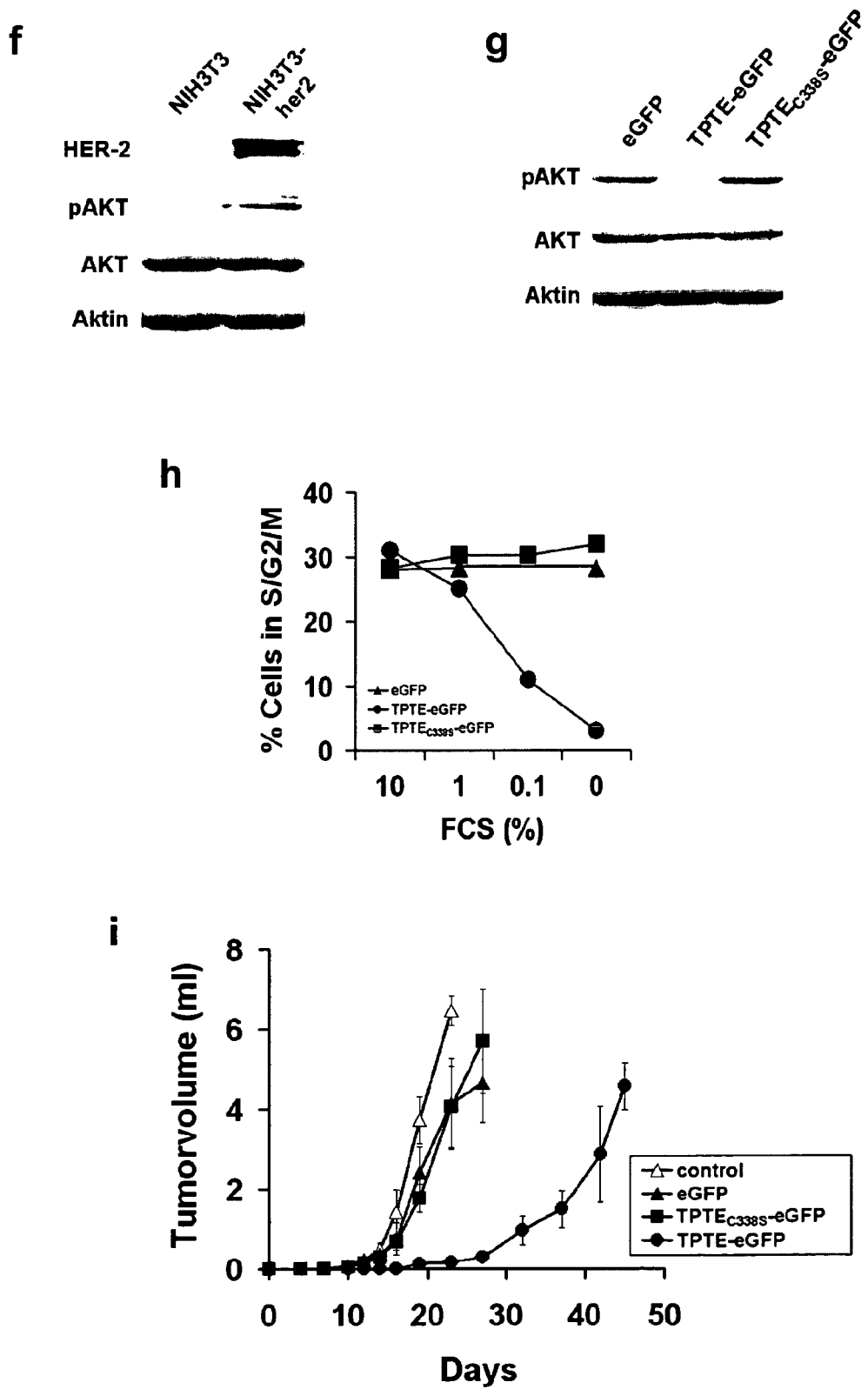

FIG. 3 TPTE Establishes a Growth-Factor Dependent Phenotype in Cancer Cells.

The influence of TPTE on AKT phosphorylation, cell proliferation and resistance to apoptosis induced by growth factor deprivation was analysed in siRNA transfected TPTE positive tumour cell lines (a-e) as well as in transformed cells ectopically expressing TPTE or the catalytically inactive mutant $TPTE^{C338S}$ and eGFP as controls (f-i). a, Downregulation of endogenous TPTE transcript levels in different cancer cell lines by TPTE specific siRNA quantified by real-time RT-PCR 24 h after transfection. b, Downregulation of TPTE protein expression in different cancer cell lines by TPTE siRNA (+) but not scrambled siRNA duplexes as control (−). c, Increase of cellular phospho-AKT levels by TPTE siRNA (+) but not scrambled siRNA duplexes as control (−). d, e, Proliferation rate and apoptotic fraction of cell lines cultured in medium supplemented with various concentrations of serum upon knock down of TPTE by siRNA. f, Western blot analysis of HER-2/neu expression and AKT phosphorylation in wild type NIH3T3 fibroblasts and HER2/neu transformed NIH3T3 cells (NIH3T3-her2). g, AKT phosphorylation in NIH3T3-her2 cells transfected with TPTE-eGFP and controls. h, Stable expression of catalytically active TPTE-eGFP abrogates autonomous growth of NIH3T3-her2 cells as determined by flowcytometric cell cycle analysis. i, Tumour growth kinetics after s.c. inoculation of stably transfected NIH3T3-her2 cells in immunocompromised mice.

Figure 4:
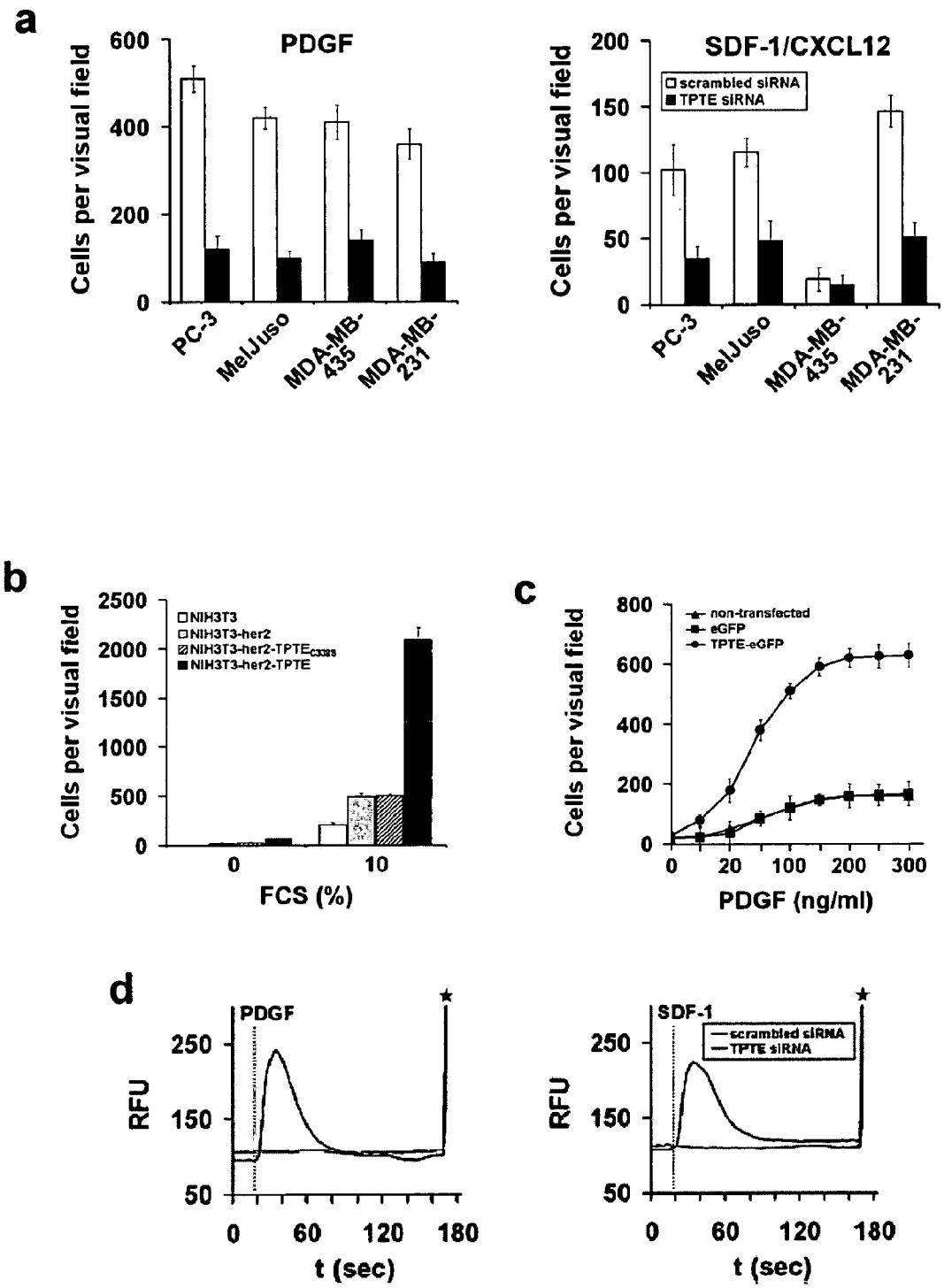
Figure 4:
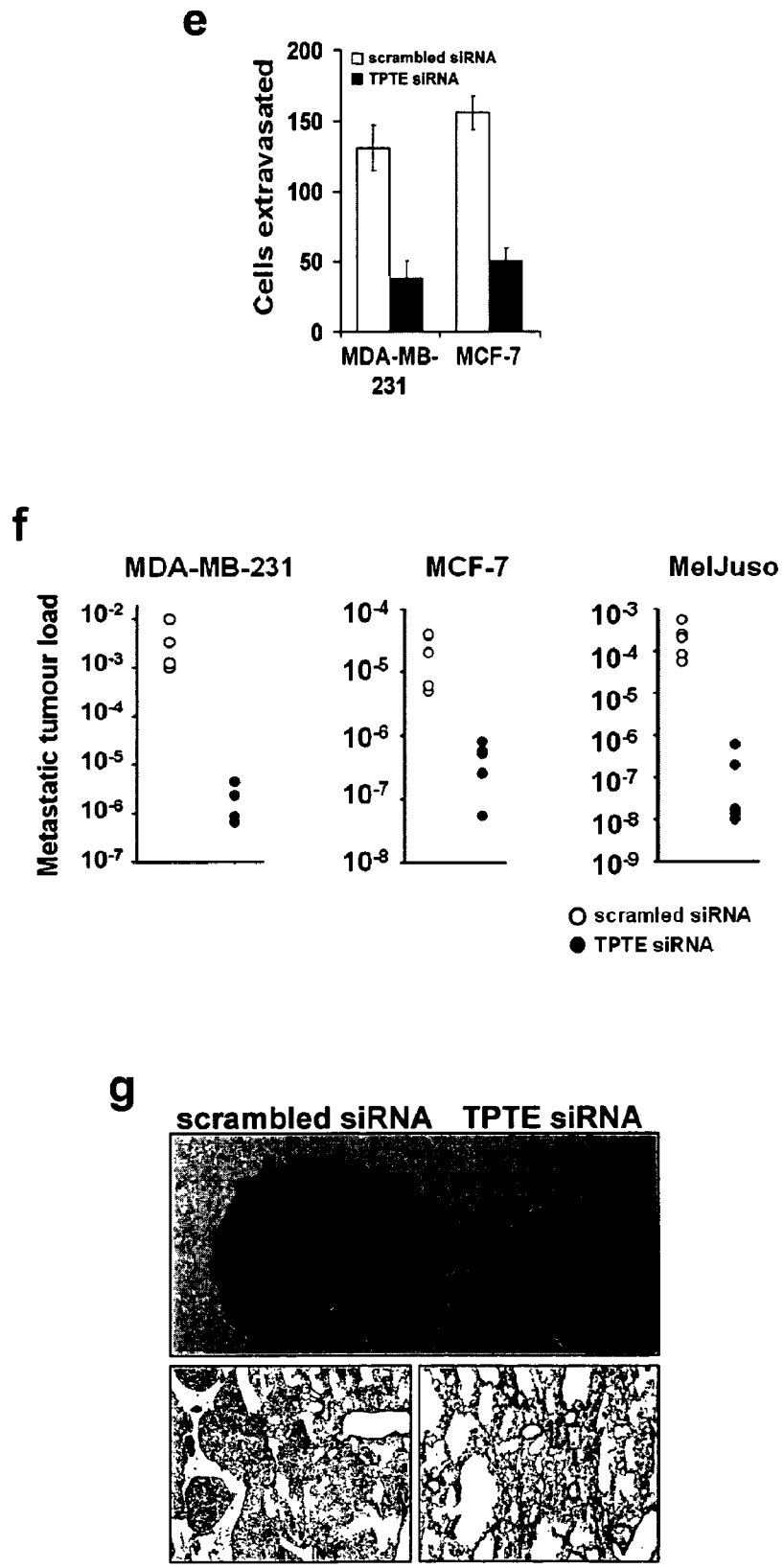

FIG. 4 Expression of TPTE Promotes Cell Chemotaxis and Metastatic Spread of Tumour Cells.

a, Transwell migration assay using PDGF-BB (200 ng/ml) and SDF-1a/CXCL12* (200 ng/ml) as chemoattractants 48 h after transfection of cells with siRNA oligos; (*MDA-MB-435 cells do not express CXCR4, the receptor for CXCL12). b, Chemotaxis of NIH-3T3-her2 transfectants analysed in transwell migration assay using FCS as chemoattractant. c, Chemotactic sensing of NIH3T3-her2 transfectants of various concentrations of PDGF-BB analysed in transwell migration assay. d, Fluorophore assisted visualisation of PDGF-induced calcium mobilisation in MDA-MB-231 cancer cells 24 h after knock down of TPTE by siRNA; asterisk, intracellular calcium stores were released from cells following calcium ionophore (ionomycine) stimulation in order to confirm cell responsiveness. e, f, Experimental metastasis assay based on injection of TPTE siRNA treated and labelled metastases forming cells into the tail-vein of NOD/SCID (MDA-MB-231) or nude (MCF-7, MelJuso) mice. Labelled cells extravasated into the lungs were counted 6 h after injection (e). Tumour load in lungs of mice was quantified by real-time PCR several weeks after inoculation (f). g, Representative lungs and HE-stained lung tissue sections obtained by an independent experiment from nude mice four weeks after inoculation with MDA-MB-231 cells.

EXAMPLE 1

Materials and Methods

Tissues and Cell Lines

This study was approved by the local ethical review board ("Ethikkommission der Ärztekammer des Landes Rheinland-Pfalz"). Recombinant DNA work was done with the official permission and according to the rules of the state government of Rheinland-Pfalz. Tissues were obtained as human surplus materials during routine diagnostic work-up or therapeutic procedures and were stored at −80° C. until use. If not otherwise stated, cell lines were obtained from commercial providers. For demethylation studies cells were split to 20-30% confluency and cultured with 2 µM or 10 µM 5-Aza-2'-deoxycytidine (5-Aza-dC) (Sigma-Aldrich) for 72 h. Colon cancer cell lines HCT116WT, HCT116DNMT1−/−, HCT116DNMT3b−/− and HCT116DKO were a generous gift from Bert Vogelstein.

RNA-Isolation, RT-PCR and Real-Time RT-PCR

RNA extraction, first-strand cDNA synthesis, RT-PCR and real-time RT-PCR was preformed as previously described (Koslowski, M. et al., Cancer Res. 62, 6750-6755 (2002), Koslowski, M. et al., Cancer Res. 64, 5988-5993 (2004)). For RT-PCR TPTE-specific oligonucleotides (sense 5'-TGG ATG TCA CTC TCA TCC TTG-3' (SEQ ID NO: 36); antisense 5'-CCA TAG TTC CTG TTC TAT CTG-3' (SEQ ID NO: 37), 63° C. annealing) were used in a 35 cycle PCR. Real-time quantitative expression analysis was performed in triplicates using TPTE-specific oligonucleotides (sense 5'-GAG TCT ACA ATC TAT GCA GTG-3' (SEQ ID NO: 38); antisense 5'-CCA TAG TTC CTG TTC TAT CTG-3' (SEQ ID NO: 37), 63° C. annealing) in a 40 cycle PCR. After normalization to 18sRNA (sense 5'-CGA TGC TCT TAG CTG AGT GTC-3' (SEQ ID NO: 39); antisense 5'-TAA CCA GAC AAA TCG CTC CAC-3' (SEQ ID NO: 40), 65° C. annealing) TPTE transcripts in tumour samples were quantified relative to normal tissues using ΔΔCT calculation.

Antisera, Immunochemistry and Western Blot

Polyclonal antiserum pAK2091 raised against the N-terminus (aa 1-51) of TPTE was obtained from a custom antibody service (SeqLab). Immunohistochemistry was performed on formalin-fixed and paraffin-embedded tissue sections after antigen retrieval. The latter procedure consisted of boiling the slides for 15 minutes in citrate buffer (pH 6) followed by a cooling period of 15 minutes at room temperature. For Western blot analysis 60 µg of total protein extracted from cells lysed with Triton-X was used. Extracts were diluted in reducing sample buffer (Roth), subjected to SDS-PAGE and proteins were subsequently electrotransferred onto PVDF membrane (Pall). For immunostaining antibodies reactive to HER2/neu (Abcam), pAKT (Cell Signaling), AKT (Cell Signaling) and beta-Actin (Abcam) were used followed by horseradish-peroxidase conjugated goat anti-mouse and goat antirabbit antibodies (Dako). Detection of the anti-TPTE pAK2091 primary antibody was performed using the anti-rabbit Envision+ System (Dako) according to the manufacturer's instructions.

Expression of eGFP-Tagged TPTE in Eukaryotic Cells

TPTE-ORF was amplified with sense primer 5'-GAG AGA AAG CTT CCA CCA TGA ATG AAA GTC CTG ATC CGA CTG ACC T-3' (SEQ ID NO: 41) and antisense primer 5'-GAG AGA AAG CTT GAT CGG ATC CAG CTA CAA CAT CAC TGG AAG TC-3' (SEQ ID NO: 42) introducing two HindIII sites. The amplified fragment was ligated into vectors pEGFP-C1 and pEGFP-N3 (BD Biosciences). Variant $TPTE^{C338S}$ carrying a mutation in the active site of the phosphatase domain was generated by PCR-mediated site directed mutagenesis.

Immunofluorescence and Colocalisation Studies

Cells expressing TPTE either constitutionally or heterologously upon transfection with plasmids were grown on slides for 12-24 h and were fixed with 2% paraformaldehyde/0.1% saponin/PBS. Indirect immunofluorescence staining for TPTE was performed with pAK2091 polyclonal rabbit antiserum and a fluorescence-tagged secondary antibody directed against rabbit IgG. For colocalisation studies of TPTE with F-Actin permeabilised, fixed cells were stained with rhodamine-phalloidin (Molecular Probes). Expression plasmids for eGFP-tagged PH-domain of PLC-d1 and AKT for visualization of membrane bound PIP2 and PIP3 were kindly provided by Mario J. Rebecchi (Tall, E. G. et al., *Curr. Biol.* 10, 743-746 (2000)) and Julian Downward (Watton, S. J. & Downward, J., *Curr. Biol.* 9, 433-436 (1999)), respectively. Coverslips were mounted on slides in Slow-Fade (Molecular Probes) for analysis by immunofluorescence microscopy.

Immunopurification of eGFP-Fusion Proteins

Cells expressing eGFP-fusion proteins were lysed with buffer containing 1% Triton X-100 and protease inhibitors (8 µM Leupeptin, 3.3 µM Chymostatin, 2.9 µM Pepstatin A, 1 mM AEBSF-Hydrochloride) for 15 min on ice. Lysates were clarified by centrifugation for 5 min at 4° C. For preclearing the lysates were incubated with protein A Sepharose CL-4B (Sigma-Aldrich) for 1 h at 4° C. The precleared lysates were incubated with anti-eGFP antibody (Delta Biolabs) for 2 h at 4° C. followed by incubation with protein A Sepharose CL-4B for 1 h at 4° C. and precipitated by centrifugation for 2 min.

Immune complexes were washed with IP buffer (50 mM HEPES (pH 7.5), 150 mM NaCl), and resuspended in reaction buffer (100 mM HEPES (pH 7.5), 150 mM NaCl, 10 mM DTT). Proteins were separated by SDS-PAGE and analyzed by immunoblotting.

In Vitro Phosphatase Assay

Phosphatase activity of PTEN and TPTE was measured in reaction buffer containing 110 µM water-soluble phosphatidylinositol phosphate (Echelon) and immunoprecipitated proteins. Samples were incubated for 90 min at 37° C. and the amount of phosphate released from substrate was determined using a malachite green assay (Echelon). After 15 min colour development the absorbance of the samples was measured at 620 nm on a Tecan Safire reader. Each sample was analyzed as triplicate.

siRNA Duplexes

The siRNA duplexes were designed following common rules (Elbashir, S. M. et al., Nature 411, 494-498 (2001)). The TPTE siRNA duplex targeted nucleotides 1722-1742 of the TPTE mRNA sequence (NM_013315.1) and comprised of sense 5'-r(GGU ACU UGA UAA CAU UAC A)dTdT-3' (SEQ ID NO: 16) and antisense 5'-r(UGU AAU GUU AUC AAG UAC C)dGdA-3' (SEQ ID NO: 17). As control a scrambled siRNA duplex comprising of sense 5'-r(UAA CUG UAU AAU CGA CUA G)dTdT-5' (SEQ ID NO: 43) and antisense 5'-r(CUA GUC GAU UAU ACA GUU A)dGdA-3' (SEQ ID NO: 44) was used. For TPTE silencing studies cells were transfected with 100 nM siRNA duplex using RNAiFect transfection reagent (Qiagen) according to the manufacturer's instructions. All functional assays were done 24 h after transfection with siRNA duplexes.

Cell Migration

Cell migration assays were performed using Transwell chambers with 8.0 µm pore membranes (BD Biosciences). Cells used in the migration assays were cultured in serum-free medium for 12 h before onset of the experiments. In siRNA experiments cells were transferred to serum-free conditions 24 h after transfection with siRNA duplexes as described above. $4 \times 10^4$ cells in 400 µl serum-free culture medium were added to the upper chamber. The bottom chambers contained 800 µl culture medium supplemented with FCS, PDGF-BB (Sigma-Aldrich) or SDF-1a/CXCL12 (R&D Systems) as chemoattractants. Cells were allowed to migrate for 24 h. Cells that had migrated to the bottom side of the membrane were fixed in ice-cold methanol; membranes were excised, placed on microscope slides and mounted with Hoechst (Dako) for fluorescence microscopy. Cells in five random visual fields (100× magnification) were counted for each membrane. All experiments were done in triplicates.

Cell Proliferation

Proliferation was analysed using DELFIA cell proliferation Kit (Perkin Elmer) according to the manufacturer's instructions. 24 h after transfection with siRNA duplexes $1 \times 10^4$ cells were cultured in medium supplemented with varying concentrations of FCS for 48 h. Assays were measured on a Wallac Victor2 multi-label counter (Perkin Elmer)

Cell Cycle Analysis and Apoptosis

Cells were cultured in medium supplemented with fetal calf serum in varying concentrations, harvested after 48 h and stained with propidiumiodide prior to flowcytometric DNA content analysis. Apoptotic cells and cells in S/G2/M were quantified using CellQuest-Software (Becton Dickinson).

Calcium Mobilisation Assay

Mobilisation of intracellular calcium was analyzed using FLIPR Calcium 3 Assay Kit (Molecular Devices). $2 \times 10^4$ cells were cultured in serum-free medium for 12 h in clearbottom 96 well plates. After fluorophore labelling according to the manufacturer's instructions cells were stimulated with 100 ng/ml PDGF-BB (Sigma-Aldrich) or 100 ng/ml SDF-1a/CXCL12 (R&D Systems) in triplicates. Calcium mobilisation was documented using Olympus-IX71 inverted microscope and TILLvisION software (TILL Photonics).

In Vivo Tumour Growth Analysis and Experimental Metastasis Assay $5 \times 10^6$ cells (NIH3T3-her2, NIH3T3-her2-eGFP, NIH3T3-her2-TPTE-eGFP, and NIH3T3-her2-TPTE$^{C338S}$-eGFP) were injected subcutaneously into the flanks of NOD/SCID mice (5 animals per group) for tumour growth analysis. Tumours were measured periodically with a caliper rule, and the tumour volume was calculated (V=axbxb/2). For assessment of tumour cell extravasation $1 \times 10^6$ labelled with CFSE (Vybrant CFDA SE Cell Tracer Kit; Molecular probes) cells were injected into the tail vein of NOD/SCID mice (3 animals per group). Mice were sacrificed after 6 h and Hoechst 33258-labelled cryosections (20 µM) of the lungs were analysed for extravasated tumour cells using fluorescence microscopy (Voura, E. B. et al., *Nat. Med.* 10, 993-998 (2004)). Tumour cells in 50 random visual fields per lung were counted. Quantification of the tumour load in the lungs of NOD/SCID mice (4 animals per group) was done by real-time PCR five weeks after i.v. injection of $2 \times 10^6$ MDA-MB-231 cells. DNA was extracted using QIAamp DNA Mini Kit (Qiagen). A 226 bp fragment of the a-satellite region of the human chromosome 17 (sense 5'-CAG CTG ACT AAA CAG AAG CAG-3' (SEQ ID NO: 45); antisense 5'-GAG TTG AAT GCA GTC ATC ACA G-3' (SEQ ID NO: 46)) was amplified using 1 µg DNA, respectively. The tumour load was quantitated with reference to a standard curve generated by a serial dilution of MDA-MB-231 cells in NIH3T3 mouse fibroblasts.

Statistical Analysis

Statistical analysis of TPTE expression in tumours in relation to the metastatic rate of the patients was performed using SPSS software (Fisher's exact test).

EXAMPLE 2

TPTE is Ectopically Expressed in Human Tumours

We first investigated TPTE mRNA expression in a large set of normal and neoplastic tissue specimens. TPTE expression is confined to testis and transcript amounts are below detection limit of highly sensitive RT-PCR in all other normal tissue specimens (FIG. 1a,b). In contrast, we detected strong TPTE expression in 59 of 155 (38%) tumour samples across different cancer types including malignant melanoma (50%), breast carcinomas (47%) and lung carcinomas (55%) as well as in a large set of cancer cell lines (62%) (Tab. 1).

TABLE 1

Expression of TPTE in human tissues and cell lines analyzed by RT-PCR and Real-Time PCR.

| | Positive/tested |
|---|---|
| Normal tissues | |
| Testis | 3/3 |
| Small intestine | 0/2 |
| Colon | 0/3 |
| Liver | 0/2 |
| Lung | 0/3 |
| Lymph node | 0/2 |
| Stomach | 0/2 |
| Spleen | 0/2 |
| Adrenal gland | 0/1 |
| Kidney | 0/3 |
| Esophagus | 0/1 |
| Ovary | 0/2 |
| Thymus | 0/1 |
| Skin | 0/2 |
| Breast | 0/3 |
| Pancreas | 0/2 |
| PBMC's, resting | 0/3 |
| PBMC's, proliferating | 0/3 |
| Prostate | 0/2 |
| Thyroid | 0/2 |
| Endometrium | 0/3 |
| Cerebellum | 0/1 |
| Brain | 0/2 |
| Tumour tissues | |
| Breast cancer | 17/36 (47%) |
| Lung cancer | 25/45 (55%) |
| Malignant melanoma | 9/18 (50%) |
| Colon cancer | 0/20 |
| Prostate cancer | 3/8 |
| Ovarian cancer | 2/7 |
| Cervical cancer | 1/6 |
| Tumour cell lines | |
| Breast cancer cell lines | 4/5 |
| Lung cancer cell lines | 2/6 |
| Melanoma cell lines | 5/8 |
| Prostate cancer cell lines | 2/2 |

A polyclonal rabbit antibody (pAK2091) against the N-terminus (aa 1-51) of TPTE was used to verify expression data at the protein level. In accordance with the predicted size of TPTE, a 65 kDa band was detected by Western blot analysis in testicular tissue, in a number of tumor cell lines typed positive for constitutive TPTE expression by RT-PCR, as well as in cells transfected with TPTE-cDNA confirming specificity of the antibody (FIG. 1c, left). In agreement with RT-PCR data, normal somatic tissues scored negative in Western blot for TPTE, whereas TPTE RT-PCR positive cancer tissues contain significant amounts of TPTE protein (FIG. 1c, right). Immunohistochemistry with pAK2091 on testicular tissue showed specific immunoreactivity in type II spermatocytes and prespermatids in agreement with in situ hybridisation data described recently for the mouse orthologue (Wu, Y. et al., J. Biol. Chem. 276, 21745-21753 (2001)) (FIG. 1d). Tissue specimens obtained from cancers of lung, breast and prostate as well as malignant melanomas displayed a strong tumour cell-specific staining in immunohistochemistry. In contrast, adjacent stromal and non-neoplastic epithelial cells (FIG. 1d) as well as patient matched normal tissues were not reactive (not shown). Having established TPTE as a molecular tumour marker, we proceeded to investigate the mechanism responsible for its ectopic activation in cancer cells. DNA methylation at CpG-rich promoters has been reported to be the primary mechanism for silencing of a subset of germline-specific genes in somatic tissues. Genomic demethylation, in turn, appears to be sufficient for aberrant activation of these genes in tumour cells (Koslowski, M. et al., Cancer Res. 64, 5988-5993 (2004), De Smet, C. et al., Mol. Cell. Biol. 19, 7327-7335 (1999), De Smet, C. et al., Mol. Cell. Biol. 24, 4781-4790 (2004)). In fact, TPTE transcription was robustly induced upon treatment of several non-expressing cancer cell lines with the DNA methylation inhibitor 5-Aza-2'-deoxycytidine (FIG. 1e). Methylation-dependent regulation of TPTE transcription was further evaluated in wild type HCT116 colon cancer cells and descendants with disrupted DNA methyltransferase (DNMT) genes. HCT116WT cells as well as the DNMT3b-/- and DNMT1-/- single knockout variants, which are known to display almost normal or only moderately reduced global DNA methylation (Rhee, I. et al., Nature 416, 552-556 (2002)), do not express TPTE. In contrast, HCT116DKO cells lacking both methyltransferases and exhibiting vastly diminished overall DNA methylation showed a robust induction of TPTE expression (FIG. 1e). Both assays independently confirmed that DNA methylation is necessary for TPTE silencing and that genomic demethylation as frequently observed in tumours (Ehrlich, M., Oncogene 21, 5400-5413 (2002), Feinberg, A. P. & Vogelstein, B., Nature 301, 89-92 (1983)) is sufficient for its activation.

EXAMPLE 3

TPTE is a Plasma Membrane PIP3-Phosphatase

TPTE contains a phosphatase as well as a lipid-binding C2 domain. Both structural features have been shown to be essential and sufficient for the lipid phosphatase activity of its homologue PTEN (Wu, Y. et al., J. Biol. Chem. 276, 21745-21753 (2001), Lee, J. O. et al., Cell 99, 323-334 (1999)). Whereas a lipid phosphatase activity with substrate-specificity for $PIP_3$ and $PI(3,4)P_2$ has previously been shown for the mouse orthologue of TPTE (Wu, Y. et al., J. Biol. Chem. 276, 21745-21753 (2001)) in vitro, a lack of significant enzymatic activity was reported for human TPTE (Walker, S. M. et al., Biochem. J. 360, 277-283 (2001)). Since the latter study used recombinant protein of bacterial origin, we reassessed enzymatic activity of human TPTE with eucaryotically produced protein. To this end, we expressed the phosphatase and C2 domains of TPTE and PTEN fused to eGFP in HEK-293 cells, purified the proteins by immunoprecipitation with anti-eGFP antibody coupled protein A beads and used them in a malachite green assay. Equimolar amounts of immunoprecipitates obtained from cells transfected with eGFP or with $TPTE^{C338S}$-eGFP, a TPTE variant mutated at a site critical for the putative phosphatase activity, served as controls to rule out contamination with copurifying phosphatases. Surprisingly, we found that TPTE releases phosphate specifically from $PIP_3$ at a rate comparable to PTEN. Lack of phosphatase activity in $TPTE^{C338S}$-eGFP and eGFP controls confirmed the specificity of the assay (FIG. 2a). This finding together with the aberrant activation of TPTE in human cancers indicates that TPTE is involved in phosphoinositide-mediated plasma membrane signalling events in tumour cells.

TPTE-negative cells transfected with TPTE-eGFP as well as cancer cell lines, which express TPTE constitutively were labelled with anti-TPTE antibody and investigated by immunofluorescence microscopy. In addition to the previously described localization to Golgi apparatus and endoplasmatic reticulum (Wu, Y. et al., *J. Biol. Chem.* 276, 21745-21753 (2001)), we found a major portion of TPTE at the plasma membrane (FIG. 2*b*, 2*c*). TPTE appears accentuated at membrane ruffles and at lateral margins of membrane protrusions including pseudopodia and filopodia, whereas the tips of such structures remain free of TPTE (FIG. 2*d*). Costaining of these cells with rhodamine-phalloidin, a marker for F-actin, showed a colocalisation of plasma membrane TPTE with filamentous actin (FIG. 2*e*). To dissect the spatial association of TPTE with plasma membrane phosphoinositides we performed colocalisation studies with pleckstrin domain-eGFP fusion proteins using the PLC-d1-PH (phosholipase C-d1 pleckstrin homology) (Tall, E. G. et al., *Curr. Biol.* 10, 743-746 (2000)) and the AKT-PH (Watton, S. J. & Downward, J., *Curr. Biol.* 9, 433-436 (1999)) domains, which selectively bind to either $PIP(4,5)P_2$ or 3'-phosphorylated phospholipids, respectively. Remarkably, staining of cells coexpressing TPTE cDNA and eGFP-tagged PH-domains with pAK2091 demonstrated an almost complete overlap of TPTE with PLC-d1-PH-eGFP (FIG. 2*f*) but not with AKT-PH-eGFP (not shown), establishing that TPTE colocalises with $PIP_2$ (FIG. 2*f*). Cotransfection with TPTE cDNA but not $TPTE^{C338S}$-cDNA resulted in a complete redistribution of AKT-PH-eGFP from the plasma membrane to the cytosol in HER-2/neu transformed fibroblasts (Schiffer, I. B. et al., *Cancer Res.* 63, 7221-7231 (2003)), proving that TPTE decreases plasma membrane $PIP_3$ levels. Altogether these observations imply that TPTE is involved in spatial control of plasma membrane phosphoinositides, metabolises $PIP_3$ and binds to PIP2 as previously demonstrated for PTEN (Iijima, M. et al., *J. Biol. Chem.* 279, 16606-16613 (2004)).

EXAMPLE 4

Use of siRNA in Silencing TPTE Expression

We analysed the effects of small interfering RNA (siRNA) induced gene silencing of TPTE in breast cancer, prostate cancer and malignant melanoma cell lines, which endogenously express the tumour-associated phosphatase TPTE. Quantitative RT-PCR and Western blot demonstrated that TPTE specific siRNA duplexes induce a robust knockdown of TPTE transcripts and protein without affecting cellular PTEN levels (FIG. 3*a*, 3*b*).

In addition, we used transformed fibroblasts stably transfected with either TPTE or the catalytically inactive $TPTE^{C338S}$ variant, to clarify the effects directly induced by the phosphatase activity of the molecule. First, we quantified levels of Ser473 phosphorylated AKT (pAKT) as a measure of cellular $PIP_3$ signalling. siRNA-mediated knockdown of TPTE resulted in a substantial upregulation of cellular pAKT in all tumour lines tested (FIG. 3*c*) demonstrating that endogenous TPTE significantly counteracts constitutive PI3K overactivation in cancer cells. In concordance with this observation, suppression of TPTE in tumour cells has a substantial impact on cellular processes controlled by pAKT signalling. TPTE silencing is associated with a reduced growth factor-dependency of tumour cells giving rise to an autonomous phenotype with sustained proliferation rates (FIG. 3*d*) and protection from apoptosis even under serum starvation (FIG. 3*e*). Consistent with the biological consequences of permanent AKT activation (FIG. 3*f*), HER-2/neu transformed NIH3T3 cells (NIH3T3-her2) display a resistance to apoptosis and exhibit sustained proliferation even under growth-factor starvation. Expression of TPTE but not mutated $TPTE^{C338S}$ in these transformed fibroblasts resets proliferation and survival autonomy and results in reduced pAKT levels (FIG. 3*g*), a strictly serum-dependent proliferation and rapid onset of a G0/G1 cell cycle block upon growth factor removal (FIG. 3*h*). Notably, NIH3T3-her2 cells expressing TPTE are still tumorigenic in immunocompromised mice. However, tumour growth was markedly reduced compared to controls lacking the phosphatase activity (FIG. 3*i*). These findings demonstrate that TPTE balances upstream oncogene-induced PI3K overactivation and renders tumour cell growth and survival dependent on external growth factors without abrogating tumourigenecity.

EXAMPLE 5

TPTE Promotes Tumour Cell Chemotaxis

TPTE specific siRNA duplexes but not control duplexes reduced tumour cell migration towards PDGF and SDF-1/CXCL12 gradients in all tumour cell lines tested in transwell migration assays (FIG. 4*a*), indicating an essential role of TPTE in tumour cell chemotaxis to different classes of chemoattractants. Moreover, we made the observation that TPTE but not its catalytically inactive mutant variant potentiates HER-2/neu effects on cell migration. The increased baseline migration rate of NIH3T3-her2 cells owing to transformation by this oncogene (McCulloch, P. et al., *Eur. J. Surg. Oncol.* 23, 304-309 (1997)) is further augmented upon coexpression of TPTE (FIG. 4*b*). Such double positive cells migrate efficiently even towards lowest gradients of chemoattractants (FIG. 4*c*) indicating that a combination of PI3K overactivation and TPTE expression promotes both chemokine sensing and efficient chemotactic migration. In line with this, expression of TPTE but not $TPTE^{C338S}$, results in profound morphological changes, i.e. the transition from a rounded cell shape to a polarized, polymorphic phenotype and induction of pseudo- and filopodia. As we showed for constitutively expressing cancer cell lines (FIG. 2*d*), TPTE is strongly enriched in these protrusions suggesting that the lipid phosphatase is directly involved in the generation of filopodial extensions. To further explore alterations in chemokine and growth factor signalling we determined calcium mobilisation kinetics of tumour cells in response to chemoattractants. Fluorophore assisted visualisation of intracellular calcium concentrations demonstrated that siRNA induced TPTE downregulation almost completely abrogates PDGF and SDF-1/CXCL12 induced calcium mobilisation in cancer cells (FIG. 4*d*) thereby further substantiating a crucial role for TPTE in a proper chemotactic response of tumour cells. Chemotaxis mediated by growth factor receptors like EGF (Price, J. T. et al., *Cancer Res.* 59, 5475-5478 (1999)) and PDGF (Heldin, C. H. & Westermark, B., *Physiol Rev.* 79, 1283-1316 (1999)) or chemokine receptors such as CXCR4 and CCR7 (Muller, A. et al. *Nature* 410, 50-56 (2001)) promotes cancer invasion and metastasis. We assessed whether the strong promigratory activity of TPTE observed in vitro is of relevance for the natural course of malignant disease in vivo, in particular with regard to metastatic spread of tumours. To this end, we typed samples from 34 breast cancer patients from a thoroughly characterized cohort (Ahr, A. et al., *Lancet* 359, 131-132 (2002)) and 24 non-small cell lung cancer specimens by realtime RT-PCR for TPTE expression. There was no significant correlation between TPTE expression and tumour stage or differentiation grade. However, we found a striking, statistically highly significant correlation between expression of TPTE and metastatic disease (Tab. 2).

TABLE 2

Correlation of TPTE expression and presence of metastases.

| TPTE | | Lymph node metastasis | | Distant metastasis | |
|---|---|---|---|---|---|
| | Expression | N− | N+ | M− | M+ |
| Breast cancer N = 34 | − | 10 (29%) | 7 (21%) | 17 (50%) | 0 |
| | + | 4 (12%) | 13 (38%) | 14 (41%) | 3 (9%) |
| Lung cancer (NSCLC) N = 24 | − | 6 (17%) | 2 (6%) | 8 (33%) | 0 |
| | + | 4 (12%) | 12 (35%) | 12 (50%) | 4 (17%) |
| Total N = 58 | − | 16 (28%) | 9 (15%) | 25 (43%) | 0 |
| | + | 8 (14%) | 25 (43%) | 26 (45%) | 7 (12%) |
| | | P < 0.003 | | P < 0.02 | |

Remarkably, 12% of the patients with TPTE positive primary tumours had metastases to other organs at the time of diagnosis, whereas all patients with TPTE negative tumours were free of metastases (P<0.02). The correlation for lymph node metastases was even more significant with 76% in the TPTE positive group as compared to 36% in the negative group (P<0.003). Finally, to substantiate a direct role of TPTE in metastasis, we studied tumour cell extravasation, which is a critical step for metastatic dissemination of tumour cells mediated by chemotaxis. siRNA treated, fluorophore-labelled MDA-MB-231 and MCF-7 breast cancer cells were injected into the tail vein of immunocompromised mice. Six hours later animals were sacrificed and the number of tumour cells extravasated into the lungs was quantified in whole mount lung sections by fluorescence microscopy. For both tumour cell lines siRNA mediated knockdown of TPTE significantly reduced the number of extravasated cells (FIG. 4e). Furthermore, investigation of lungs of mice several weeks after inoculation with metastases forming MDA-MB-231, MCF-7, and MelJuso cells revealed a profound reduction of the metastatic tumour load for cells transfected with TPTE siRNA as compared to controls (FIG. 4f). Independently, experimental metastases assays with MDA-MB-231 in nude mice giving rise to macroscopic lesions confirmed these striking findings and proved a crucial role of TPTE for metastatic dissemination (FIG. 4g).

Together, these experiments demonstrate that TPTE essentially promotes extravasation and metastatic spread of cancer cells.

The invention claimed is:

1. An isolated siRNA comprising
a sense RNA strand from about 17 to about 29 nucleotides in length; and
an antisense RNA strand from about 17 to about 29 nucleotides in length, wherein the sense and antisense RNA strands form an RNA duplex, and wherein the sense RNA strand comprises a nucleotide sequence substantially identical to a target sequence having a nucleic acid sequence of nucleotide positions 3-21 of SEQ ID NO: 15.

2. The siRNA of claim 1, wherein said sense RNA strand has the sequence of SEQ ID NO: 16 and said antisense RNA strand has the sequence of SEQ ID NO: 17.

3. The siRNA of claim 1, wherein said TPTE mRNA comprises a nucleic acid sequence which is selected from the group consisting essentially of:
SEQ ID NOs: 1, 2, 3, 4, 5, 7 and, a part thereof.

4. The siRNA of claim 1, wherein said siRNA molecule is assembled from two nucleic acid fragments wherein one fragment comprises the sense strand and the second fragment comprises the antisense strand of said siRNA molecule.

5. The siRNA of claim 1, wherein the sense and antisense RNA strands forming the RNA duplex are covalently linked by a single-stranded hairpin.

6. The siRNA of claim 1, wherein the siRNA further comprises non-nucleotide material.

7. The siRNA of claim 1, wherein the sense and antisense RNA strands are stabilized against nuclease degradation.

8. The siRNA of claim 1, further comprising a 3'-overhang.

9. The siRNA of claim 8, wherein the 3'-overhang comprises from 1 to about 6 nucleotides.

10. The siRNA of claim 8, wherein the 3'-overhang comprises about 2 nucleotides.

11. The siRNA of claim 8, wherein the sense RNA strand comprises a first 3'-overhang, and the antisense RNA strand comprises a second 3'-overhang.

12. The siRNA of claim 11, wherein the first and second 3'-overhangs independently comprise from 1 to about 6 nucleotides.

13. The siRNA of claim 12, wherein the first 3'-overhang comprises a dinucleotide and the second 3'-overhang comprises a dinucleotide.

14. The siRNA of claim 13, where the dinucleotide is dideoxythymidylic acid or diuridylic acid.

15. The siRNA of claim 8, wherein the 3'-overhang is stabilized against nuclease degradation.

16. An expression vector comprising nucleic acid sequences for expressing a sense RNA strand, an antisense RNA strand, or both of a siRNA according to claim 1.

17. The expression vector of claim 16, wherein said vector is a recombinant viral vector.

18. A pharmaceutical composition comprising the siRNA of claim 1 or the expression vector of claim 16 and a pharmaceutically compatible carrier.

19. An RNA duplex comprising
a sense RNA strand from about 17 to about 29 nucleotides in length; and
an antisense RNA strand from about 17 to about 29 nucleotides in length, wherein said antisense RNA strand comprises a nucleotide sequence complementary to a target sequence having a nucleic acid sequence of nucleotide positions 3-21 of SEQ ID NO: 15.

20. The RNA duplex of claim 19, wherein said antisense RNA strand is perfectly complementary to a target sequence of about 19 or more contiguous nucleotides in TPTE mRNA.

21. An expression vector comprising nucleic acid sequences for expressing a sense RNA strand, an antisense RNA strand, or both of an RNA duplex according to claim 19.

* * * * *